United States Patent [19]
Tateno et al.

[11] Patent Number: 6,004,810
[45] Date of Patent: *Dec. 21, 1999

[54] LIVER PARENCHYMAL CELLS HAVING CLONAL GROWTH ABILITY, METHOD FOR OBTAINING SAME, METHOD FOR SUBCULTURING SAME, AND SUBCULTURING SYSTEM OF PRIMARY HEPATOCYTES

[75] Inventors: Chise Tateno; Katsutoshi Yoshizato, both of Hiroshima, Japan

[73] Assignee: Research Development Corporation of Japan, Saitama, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/419,982

[22] Filed: Apr. 11, 1995

[51] Int. Cl.$^6$ .................................................. C12N 5/06
[52] U.S. Cl. ............................................ 435/353; 435/378
[58] Field of Search ........................... 435/240.2, 240.21, 435/267, 172.3, 69.1, 29, 325, 353, 378; 935/62

[56] References Cited

U.S. PATENT DOCUMENTS

| | | | |
|---|---|---|---|
| 5,082,670 | 1/1992 | Gage et al. | 424/520 |
| 5,112,757 | 5/1992 | Guguen-Guillouzo et al. | 435/347 |

OTHER PUBLICATIONS

Brill et. al. 1993 Proc. Soc. Exp. Bio Med. vol. 204 pp. 261–269.
Mitaka et. al. 1992 Hepatology vol. 16 No. 2 440–447.
Whitaker, A.M. 1977 In CRC Handbook Series in Nutrition and Food. vol. IV. Miloslav Rechcigl (ed). CRC Press, Inc. Cleveland Ohio. pp. 31–59.
Hixson, D. et. al. 1990 Pathobiology vol. 58. 65–77.

*Primary Examiner*—James Ketter
*Assistant Examiner*—Irem Yucel
*Attorney, Agent, or Firm*—Wenderoth, Lind & Ponack, L.L.P

[57] ABSTRACT

The present invention provides liver parenchymal cells having a clonal growth ability, which possesses at least one of the cell biological properties such as: presence of peroxysome; being positive to hepatocyte-markers; being partially positive to neoplastic hepatocyte-markers or immature hepatocyte-markers; being positive to antibodies against the surface antigens of ovall cells; and being partially positive to bile duct cell-markers. The present invention also provides a method for obtaining such cells and a method for subculturing such cells.

With the liver parenchymal cells above, it will be possible to research in detail the process of development and differentiation, the mechanisms of growth and functional expression of hepatic cells, and to open up a new way to clalification of mechanisms or hepatoma and various other diseases and to development of therapeutic method against these disseases.

3 Claims, 38 Drawing Sheets

(21 of 38 Drawing Sheet(s) Filed in Color)

LIVER PARENCHYMAL CELLS HAVING CLONAL GROWTH ABILITY, METHOD FOR OBTAINING SAME, METHOD FOR SUBCULTURING SAME, AND SUBCULTURING SYSTEM OF PRIMARY HEPATOCYTES

BACKGROUND OF THE INVENTION

1. Field of the Invention

The present invention relates to liver parenchymal cells having a clonal growth ability, a method for obtaining such cells, a method for subculturing such cells, and a subculturing system of primary hepatocytes. More particularly, the present invention relates to progenitor cells culturing system of liver parenchymal cells which are useful as a material for cell biological and molecular biological research on development, differentiation and proliferation process of hepatocytes or on the carcinogenic mechanism thereof, or as medical materials for developing therapeutic techniques of various hepatic diseases.

2. Description of Related Art

An animal is a multicellular organism formed through repeated division of a fertilized egg and differentiation thereof into various structures (cell aggregates) taking charge of different functions. The individual structures composing a body of organism maintain the individual by producing cells having active differentiation ability through constant division and growth of individual cells. Therefore, in order to understand the biological facts of humans and other animals or to develop a therapeutic technique through clarification of the carcinogenic mechanism, it is believed important to analyze in detail cells composing individual structures to clarify the developing and differentiating process and the mechanism of proliferation.

A method has conventionally been established, as a means to analyze in detail cells of structures in vivo, to culture cells taken out in vitro, and causing division and growth of cultured cells to ensure survival through subcultures. While various methods of subculturing primary hepatocytes have been studied, the only actual case of subculture of primary hepatocytes so far reported is one for calf, and no case has yet been achieved as to rat and mouse. A reason is that, because hepatocytes are cultured in a serum-free medium added with various growth factors on a collagen-coated dish effective for adhesion and growth of hepatocytes, it is difficult to detach the cultured cells from the dish with a little damage, and hepatocytes treated with an enzyme such as trypsin have very serious damage. While hepatocytes cultured with a dish not coated with collagen coat and a serum-free medium can be detached with a slight damage, those cultured cells cannot continue to live or grow for a long period of time, although it may be possible to adhere them again onto the dish.

More recently, on the other hand, it has been reported that small hepatocytes growing while forming a colony appear in a culture system comprising a medium added with nicotinamide and epidermal growth factor (EGF). These small hepatocytes are confirmed to express functions of matured hepatocytes such as albumin, to be divided 2 to 3 times during the first four days, and to be partially present on the 20th day of culture in the form of cells having a growth ability. Since the colony forming frequency in such a culture system is high for hepatocytes isolated from an young rat and decreases according as the age in weeks increases, these subcultured hepatocytes are considered to be "committed progenitor cells".

In this case also, however, subculturing of cells is not satisfactory, leaving problems to be solved regarding prevention of damage. It is therefore the current situation the subculturing of hepatocytes has not as yet been established.

Furthermore, in order to understand complicated and diverse functions of hepatocytes or clarify carcinogenic mechanism thereof, it is considered essential to identify pure precursor hepatocytes (progenitor cells) for which orientation of differentiation has not yet been specified, but presence thereof has not yet been confirmed or a preferential culturing method has not been established.

For these progenitor cells, the following facts are conventionally known and the following efforts to identify them are reported. More specifically, it is reported that stem cells are developed from the foregut endoderm in the course of liver development, and these stem cells differentiate into hepatocytes and bile duct epidermal cells (Shiojiri, et al.; Cancer Research. Vol. 51, pp. 2611–2620, 1991). While there is no case of confirmation of stem cells in liver of an adult (such as rat), oval cells emerging in a precancerous state in the course toward cancer of rat can lead to either hepatocelluler carcinoma or cholangiocarcinoma. This oval cell is therefore attributable to an aberrant differentiation of stem cells present in the liver of the adult rat. Hixon, et al.(Pathobiology, Vol. 58, pp. 65–77, 1990) prepared several antibodies against surface antigens of oval cells obtained from experimental hepatocarcinogenesis. Brill, at al.(Proc. Soc. Exp. Bio. MEd., Vol. 204, pp. 261–269, 1993) selected cells conbined with these antibodies from among hepatocytes of an adult rat by means of a sorter to investigate properties of these cells. As a result, it was suggested that these cells contained hepatic progenitor cells among those combined with antibodies against surface antigens of oval cells, since cells growing and differentiating into matured hepatic cells by culturing in a medium added with additive factors, or culturing on a feeder layer of mesenchyme cells of a fetus.

Presence of hepatic progenitor cells is estimated by several pieces of evidence, but has not as yet been confirmed.

SUMMARY OF THE INVENTION

The present invention has an object to provide liver parenchymal cells having a clonal growth ability considered to contain hepatic progenitor cells. Another object of the present invention is to provide a method for obtaining such cells and a method for subculturing such cells.

Further another object of the present invention is to provide subculturing systems which permit subculturing of primary hepatocytes while growing and surviving for a long period of time.

The present invention provides liver parenchymal cells having a clonal growth ability, which possesses at least one of the cell biological properties such as:

(1) presence of peroxyzome;

(2) being positive to hepatocyte-markers;

(3) being partially positive to neoplastic hepatocyte-markers or immature hepatocyte-markers;

(4) being positive to antibodies against the surface antigens of oval cels; and (5) being partially positive to bile duct cell-markers.

The present invention provides also a method for obtaining liver parenchymal cells having a clonal growth ability, which comprises: isolating hepatic cells from liver of an adult mammal; centrifuging the hepatic cells with low speed into heavy and light fractions; and culturing small cells in the light fraction on culture medium necessary containing fetal bovine serum and ascorbic acid whereby liver parenchymal cells belonging to the small cells from a colony.

In addition, the present invention provides a method for subculturing liver parenchymel cells having a clonal growth ability, which comprises: isolating hepatic cells from liver of an adult mammal; centrifuging the hepatic cells with low speed into heavy and light fractions; culturing small cells in the light fraction on a dish with culture medium necessary containing fetal bovine serum and ascorbic acid whereby liver parenchymal cells belonging to the small cells form a colony; detaching the cells of colony from the dish with a solution of EDTA; and re-culturing the detached cells on the same medium.

Moreover, the present invention provides a subculturing system for primary hepatocytes detached from a dish with a solution of EDTA, of which medium contains nicotinamide and ascorbic acid.

In accordance with the present inventions there are provided liver parenchymal cells having a clonal growth ability considered to contain hepatic progenitor cells, a method for obtaining such cells and a method for subculturing such cells. It is accordingly possible to research in detail the process of development and differentiation of hepatic cells and the mechanisms of growth and expression of functions, and to open up a new way to clarification of mechanisms of hepatoma and various other human hepatic diseases and development of therapeutic methods against these diseases.

The present invention permits subculturing of primary hepatocytes.

BRIEF DESCRIPTION OF THE DRAWINGS

The file of this patent contains at least one color photograph. Copies of this patent with color photograph(s) will be provided by the Patent and Trademark Office upon request and payment of the necessary fee.

FIG. 12 illustrates changes with time in the area of hepatocyte clusters after subculture in cases where EGF, nicotinamide, L-ascorbic acid 2-phosphate and DMSO are removed, respectively;

DETAILED DESCRIPTION OF THE INVENTION

Figure 1A:
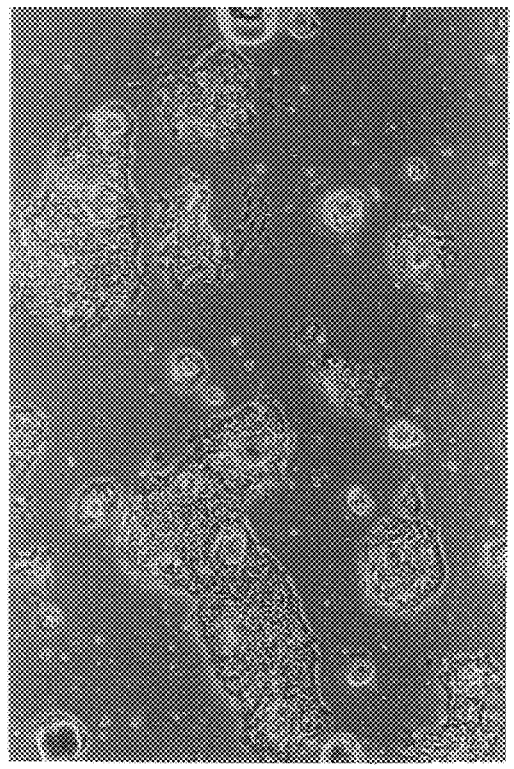
FIGS. 1(a), (b), (c) and (d) are phase contrast micrographs (29.4 magnification) illustrating examples of culture of first subculture on the second, the fifth, the eighth and the 44th days.
Figure 1B:
Figure 1C:
Figure 1D:

First, the subculturing system of the present invention is described below in detail.

More particularly, in the subculturing system of the present invention, it is possible to cause growth of hepatocytes after subculture and to maintain functions of hepatocytes for a long period of time, by adding nicotinamide and ascorbic acid into the medium of primary cells.

Conventional and other media and additives may be appropriately used. More specifically, an example is a medium system prepared by adding nicotinamide and ascorbic acid to a DMEM medium, and further adding fetal bovine serum (FBS) and epidermal growth factor (EGF).

It is needless to mention that applicable nicotinamides and ascorbic acids include, in addition to conventional ones, nicotinamide alkyls, cycloalkyls and ones having substituents, and phosphoric ester, phosphorous ester, sulfonic ester of ascorbic acid, alkyls thereof, and analogs having substituents.

Then, the method for obtaining liver parenchymal cells having a clonal growth ability of the present invention is described below in detail.

While it is the usual practice for sampling hepatocytes to obtain a heavy fraction by centrifuging at a low speed (50 G), the method of the present invention comprises separating a light fraction resulting from centrifuging at the low speed, and culturing cells contained in this light fraction. FBS and an ascorbic acid (for example, L-ascorbic acid phosphate) are added to a culture medium. As is clear from test results in the Examples described later, these constituents cause formation of colonies of small hepatocytes in the light fraction (non-parenchymal cell fraction). EGF and dimethyl sulfoxide (DMSO), not being essential for the formation of colonies, have a function of accelerating formation of colonies, and nicotinamides are considered to inhibit differentiation of hepatic cells, and are therefore preferable as constituents to be added to the culture medium. In addition to small hepatocytes, the non-parenchymal cell fraction contains endothelial cells, Kupffer cells, stellate cells and bile duct cells, which are considered to provide a special environment for small hepatocytes. The above-mentioned nicotinamides, ascorbic acids and DMSO inhibit growth of non-parenchymal cells, and permit selectively causing culturing and growth of small parenchymal cells.

The amounts of additives to the medium may be as follows: 5 to 30% FBS, 0.1 to 1.0 mM ascorbic acid, 1 to 100 ng/ml EGF, 1 to 20 mM nicotinamide, and about 0.1 to 2% DMSO.

Culture is accomplished at a temperature of about 37° C. under conditions including 5% $CO_2$.

The liver parenchymal cells thus obtained can be subcultured by detaching cells of colony from the culture dish with a solution of EDTA (0.002–0.2% EDTA) or a solution of EDTA and trypsin (0.002–0.2% EDTA and 0.005–0.5 trypsin), and then re-culturing the detached cells in the same medium as that for primary culture. Alternatively, it is possible and preferable to use the conditioned medium of the primary culture itself as the medium for subculturing. Especially, use of the conditioned medium is adequate in the case where the cells of colony being detached from the dish with the solution of EDTA/trypsin and being separating into individual cells by means of, for example, a filtration. By using these procedures, the liver paranchymal cells of the present invention can he subcultured for a long period with a state of possessing an active growth ability and properties of hepatic cells.

Through the culture as described above, colonies of small hepatocytes clonally growing are available. Expression of differentiating function of cells forming the colonies as hepatic cells can be confirmed by conducting screening by the use of at least one of such indicators as the presence of peroxyzome, being positive to hepatocyte-markers, to neoplastic hepatocute-markers, to immature hepatocyte-markers, to antibodies against the surface antigens of ovall cells, and to bile duct cell-markers. Among others, the presence of peroxisome can be confirmed by observation with a transmission electron microscope. Applicable hepatocyte-markers include such antibodies as albumin $α_1$ antitrypsin and transferrin; applicable markers of neoplastic hepatocyte or immature hepatocyte include such antibodies as GST-P and α-fetoprotein and γ-GTP stain; applicable antibodies against surface antigen of ovall cells include the antibody (OC2, OC3) prepared by Hixson et al. mentioned above; and applicable markers of bile duct cells include such antibodies as BDL (prepared by Hixson et al.) and cytokeratin 7. By using a marker for stellate cells, it is possible to identify non-parenchymal cells.

As described above, the methods of the present invention are applicable to hepatocytes of human and all other mammals, thus permitting obtaining liver parenchymal cells having a clonal growth ability from various animal species. For example, liver parenchymal cells having a clonal growth ability sampled from a human liver can be utilized for preparation of a hybrid type-artificial liver, and is expected to bring about new aspects of development of therapeutic techniques of hepatic diseases.

EXAMPLES

Now, the present invention is described in further detail by means of examples, and at the same time, properties of the subculture hepatocytes having a clonal growth ability thus obtained are described in detail with reference to test results. It is needless to mention that the present invention is not limited to the examples presented below.

Example 1

Primary hepatocytes were subcultured by using the subculturing system of the present invention.

TABLE 1 illustrates an example of configuration of the subculturing system of the present invention.

In accordance with TABLE 1, hepatic cells were isolated by the collagenase perfusion method from F344 male rats having ages ranging from four to eight weeks. The hepatic cells were cultured with a concentration of $6.7 \times 10^4$ cells/$cm^2$ on a DMEM medium added with 10% FBS, 10 ng/ml EGF, 10 mM nicotinamide, and 0.2 mM L-ascorbic acid phosphate, and 1% DMSO was added on the fourth day of culture. To detach the hepatocytes from the dish, 0.02% EDTA was used. BrdU was incorporated as an indicator of growth of the hepatocytes. The area of the hepatocyte region was measured by taking photographs periodically of the same field under a phase contrast microscope. Identification or functional expression and non-parenchymal cells was accomplished by using an immunocytochemical technique or an enzyme-cytochemical technique.

TABLE 1

F344 Rat ♂ 4~8 weeks old
↓
   Isolation of Hepatic Cells (Collagenase Perfusion)
   ↓
   Percoll Centrifugation
   ↓
   Hepatocytes
      $6 \times 10^5$ cells ./. 3.5 cm dish (without collagen coat)
      37° C., 5% $CO_2$, 95% Air
      DMEM, 44 mM $NaHCO_3$, 20 mM HEPES, 0.5 mg/l Insulin
      $10^{-7}$M Dexamethasone, 30 mg/l L prolin
      penicillin and streptmycin
   ↓ 2~3 hours
   Medium Change
      DMEM, 10% FBS, 44 mM $NaHCO_3$, 20 mM HEPES
      0.5 mg/l Insulin, $10^{-7}$M Dexamethasone
      10 mM Nicotinamide. 10 ng/ml EGF
      0.2 mM L-ascorbic acid phosphate
      penicillin and streptmycin TABLE 1-continued ↓ 4 days
Pre-confluent
   Subculture with 0.02% EDTA
      1% DMSO The same operations were carried out through systems added with additive factors such as FCS, nicotinamide, EGF, L-ascorbic acid phosphate except for one, to investigate the effects of the individual additives on the hepatocytes and the non-parenchymal cells.

Figure 1:
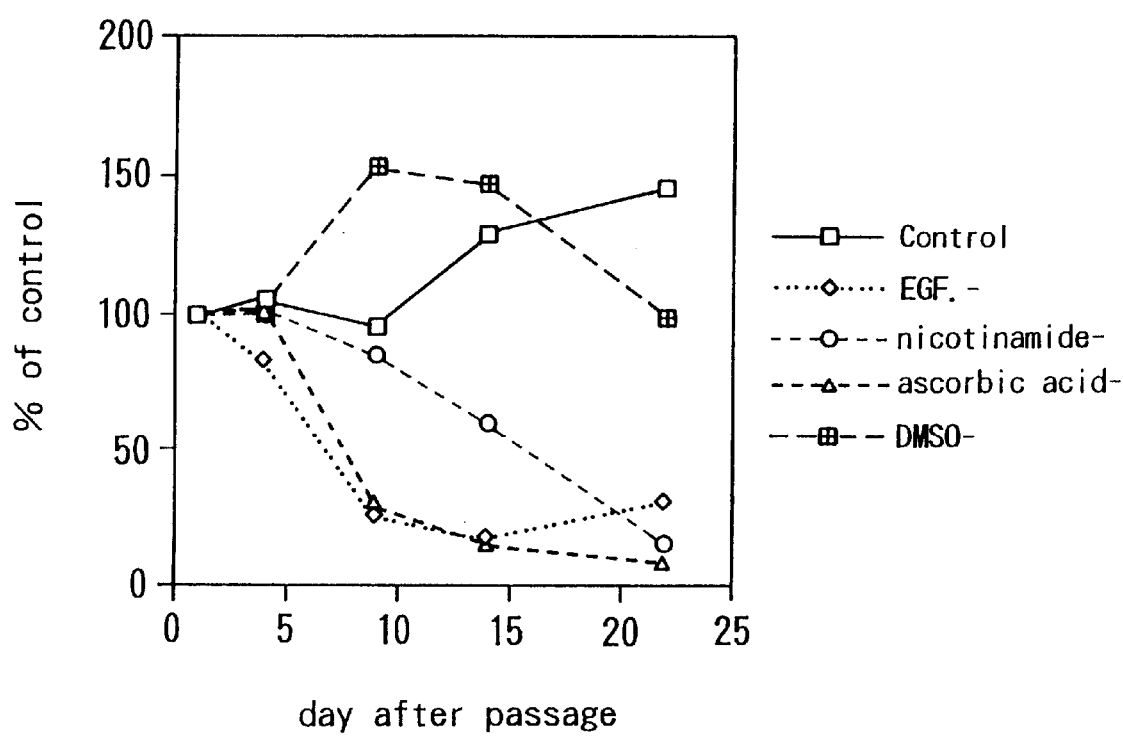

As a result of the above, a treatment with 0.02% EDTA caused the hepatocytes to detach them in the form of clusters, and as shown in FIG. 1 (first subculture×29.4), the clusters adhered to the dish within one or more days of subculture (FIG. 1(*a*): the second day of subculture), grew from the third day or so of subculture (FIG. 1(*b*): the fifth day of subculture), and part of cells died and peeled off on seventh day or so of subculture (FIG. 1(*c*): the eighth day of subculture).

Figure 2:
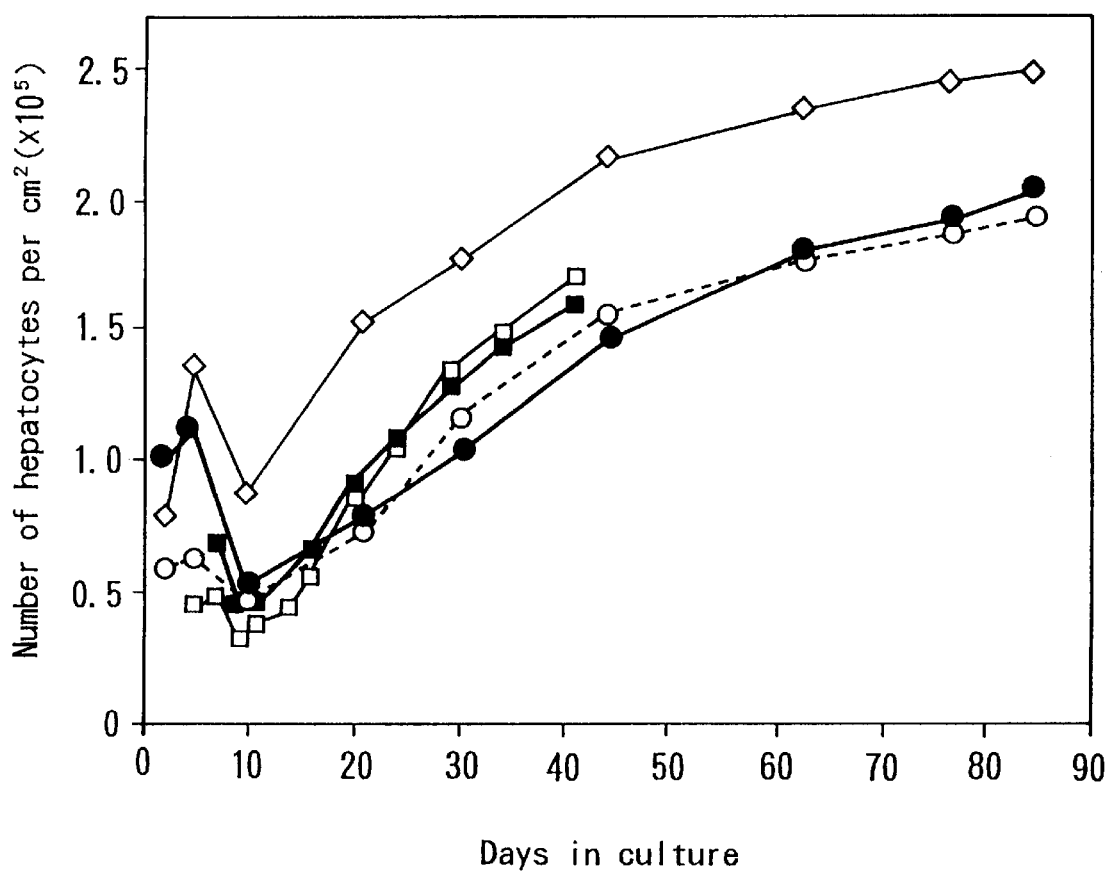
FIG. 2 illustrates an increase in number of hepatocytes.

About the eighth day or so of subculture and thereafter, the surviving hepatocytes grew (FIG. 1(*d*): the 44th day of subculture), and in the case of most proliferative clusters, the number of hepatocytes increased 5-fold on the 41th day of subculture (FIG. 2).

Figure 3A:
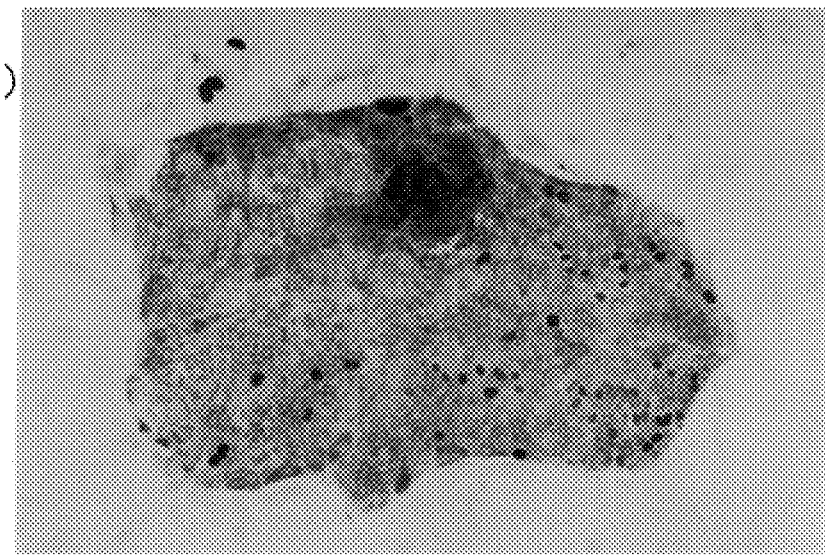
FIGS. 3(a), (b) and (c) are micrographs (100, 606 and 606 magnification, respectively) of immunocytochemistry (on the 30th, the 46th and the 50th days of first subculture, respectively) illustrating incorporation of BrdU into hepatocytes, a stain of transferrin and stains of α-antitrypsin and albumin.
Figure 3B:
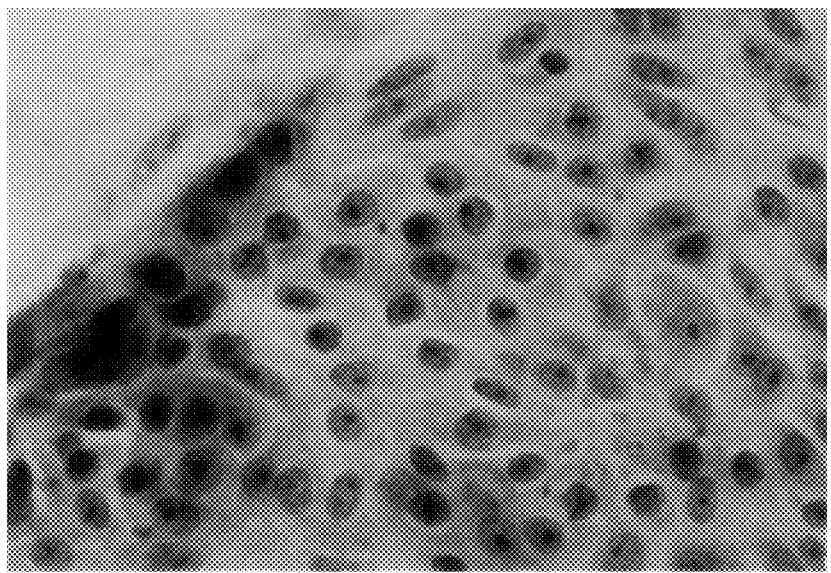
Figure 3C:
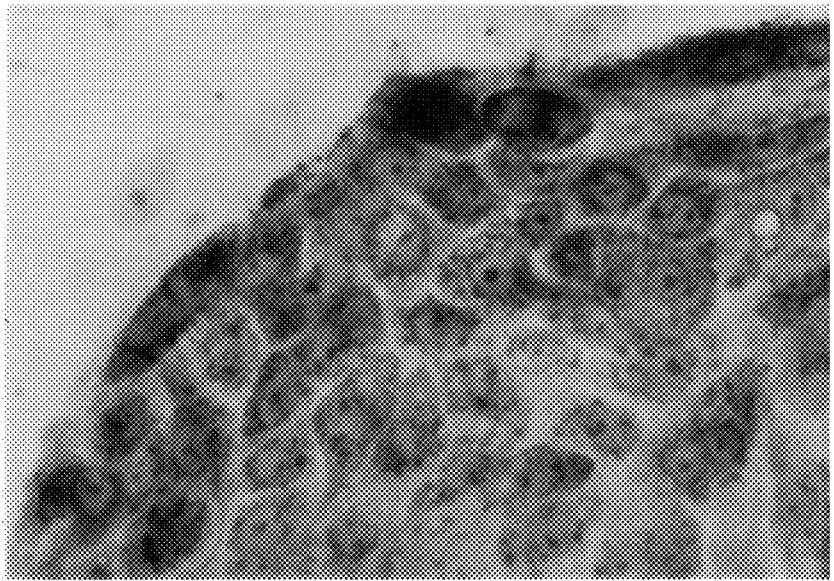
Figure 4A:
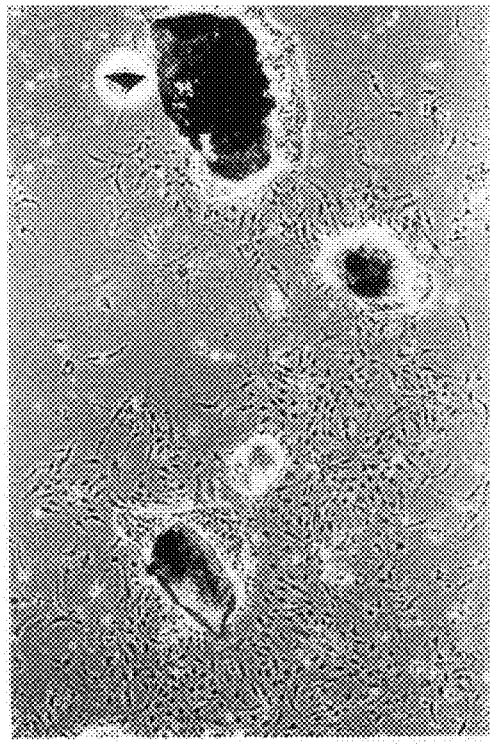
FIGS. 4(a) and 4(b) are phase contrast photomicrographs (29.4 magnification) of second subculture hepatocyte-clusters on the fourth and the 42nd days.
Figure 4B:
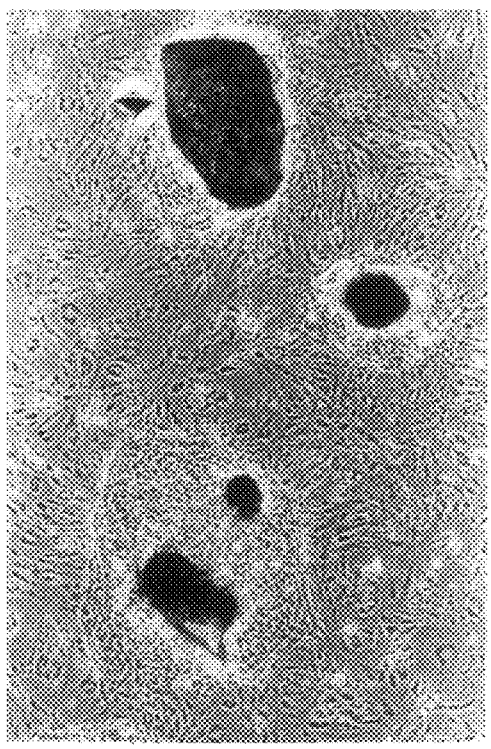
Figure 4C:
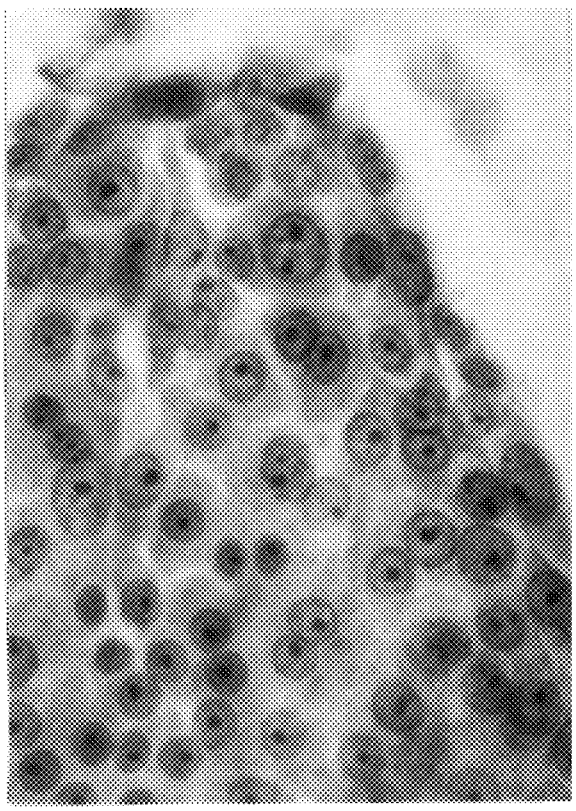
FIGS. 4(c) and 4(d) are photomicrographs (606 magnification) of immunocytochemical figures illustrating stains of albumin and transferrin, respectively, on the 52nd day.
Figure 4D:
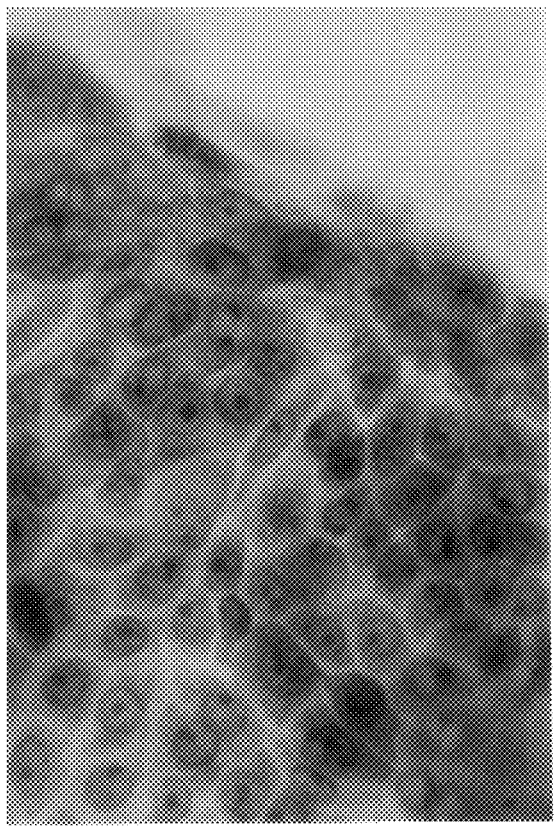

Growth of the hepatocytes after subculture was confirmed from the increase in number of the hepatocyte clusters, incorporation of BrdU, and mitotic figure. Incorporation of BrdU was observed in many hepatocytes on the 30th day of subculture (FIG. 3(*a*)). FIGS. 3(*a*), (*b*) and (*c*) show the 30th, the 45th and the 50th days of the first generation of subculture, respectively.

In FIG. 3(*a*), double staining (×100) was applied with BrdU (brown)-transferrin (red); FIG. 3(*b*) is based on stain (×606) with $α_1$-antitrypsin (brown); and in FIG. 3(*c*), staining (×606) was applied with albumin (brown). In the hepatocytes continuing to grow after subculture, expression of albumin, $α_1$-antitrypsin, and transferrin was observed.

The state of the second-generation hepatocyte clusters in subculture is illustrated in FIGS. 4(*a*), (*b*), (*c*) and (*d*). FIG. 4(*a*) shows a phase contrast figure (×30) on the fourth day of subculture, and FIG. 4(*b*) shows that on the 42nd day of subculture, both within the same field of view. FIG. 4(*c*) shows albumin (brown) staining (×606) on the 52nd day of subculture, and FIG. 4(*d*) shows transferrin (brown) staining (×606) on the 52nd day of subculture. Detaching the hepatocytes on the 35th day of subculture with 0.02% EDTA permitted observation of growth of the hepatocytes adhering again to the dish. The second-generation hepatocyte clusters in subculture were positive to albumin and transferrin.

Figure 5A:
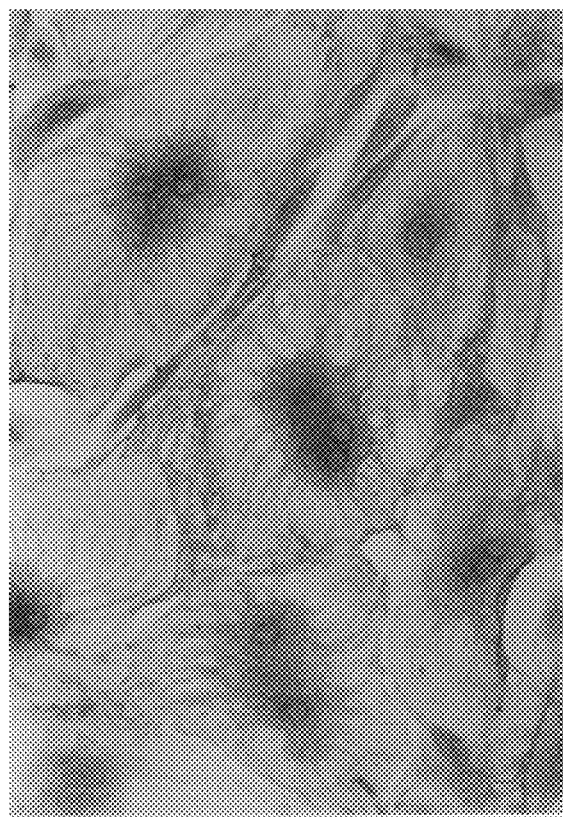
FIGS. 5(a) and (b) are photomicrographs (200 and 242 magnification) of desmin immunocytochemical figure illustrating the state of non-parenchymal hepatic cells of the first subculture on the 30th day, and esterase enzyme-cytochemical figure on the 38th day.
Figure 5B:
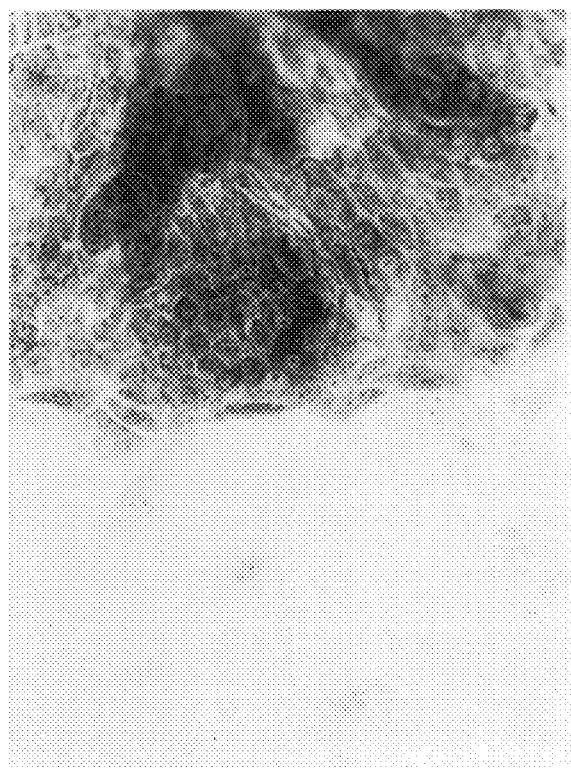

As shown, for example, in FIG. 5(*a*) illustrating the confirmation of positivity in desmin (brown) staining (×200) on the 30th day of subculture, and in FIG. 5(*b*) illustrating the confirmation of negativity (although the hepatic cells are partially positive) in esterase (brown) staining (×242) on the 38th day of subculture, non-parenchymal cells began growing around the hepatocyte clusters on the fourth day of subculture, and on the 30th day, the hepatocyte clusters were almost completely surrounded. These non-parenchymal cells, being highly positive in desmin, were considered to be stellate cells. These were not considered to be Kupffer cells because esterase activity was negative.

Figure 6:
FIG. 6 is a phase contrast photomicrograph (76 magnification) of a first subculture on the 32nd day illustrating the hepatic cord-like structure of hepatocytes.

As is clear from FIG. 6 (×76) showing the hepatic cord-like structure of the hepatocytes as a phase-contrast figure on 32nd day of subculture (first generation of subculture), a maltilayered structure of the hepatocytes was observed after the subculture, and a sequence suggesting a hepatic cord-like structure was partially observed.

Figure 7A:
FIGS. 7(a) and (b) are a phase contrast photomicrograph (29.4 magnification) illustrating the state on the 15th and 22nd days of first subculture as a control, and a photomicrograph (30 magnification) of a transferrin immunostaining figure, respectively.
Figure 7B:
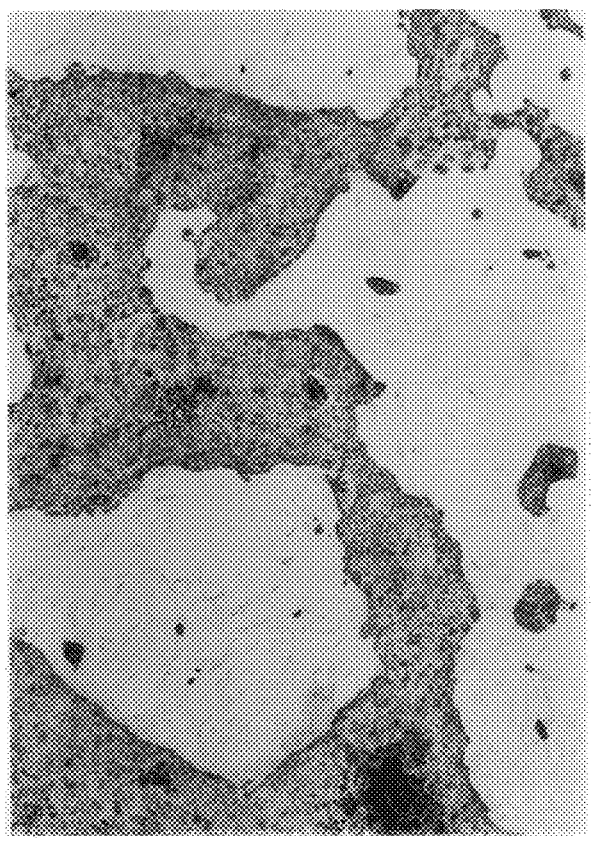
Figure 8A:
FIGS. 8A and 8B are photomicrographs illustrating the effects on hepatocytes and non-parenchymal hepatic cells when removing EGF corresponding to FIGS. 7A and 7B.
Figure 8B:
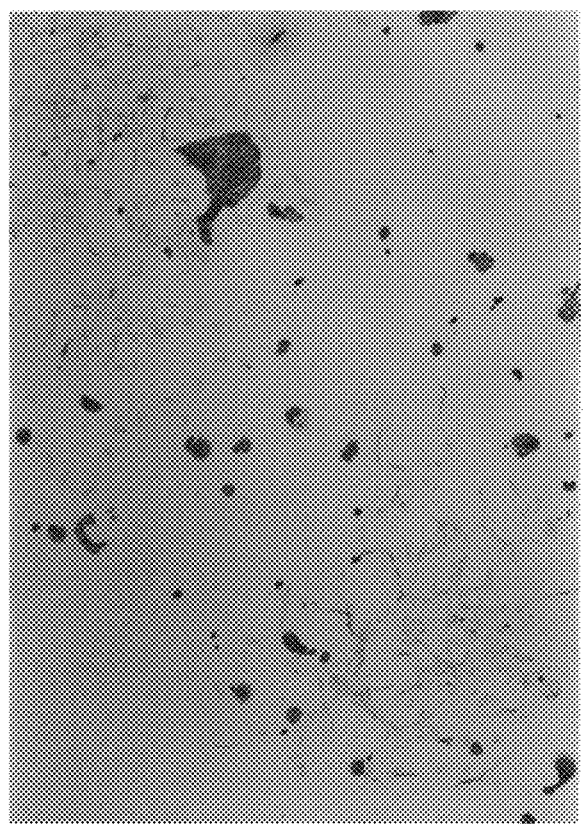
Figure 9A:
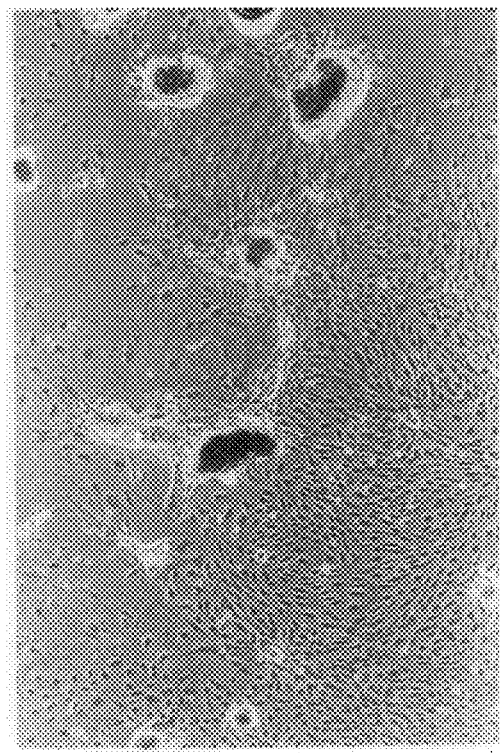
FIGS. 9A and 9B are photomicrographs of a case similar to that shown in FIGS. 7A and 7B, in which nicotinamide is removed.
Figure 9B:
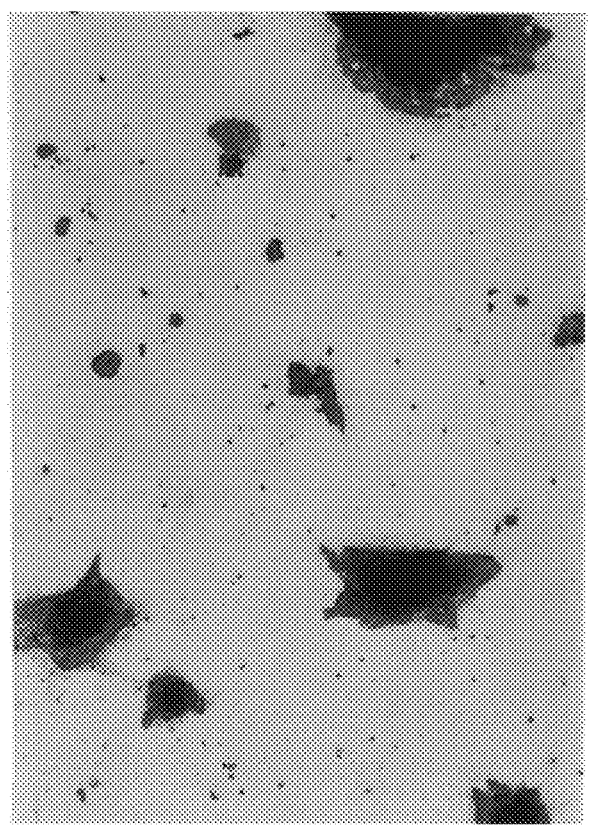
Figure 10A:
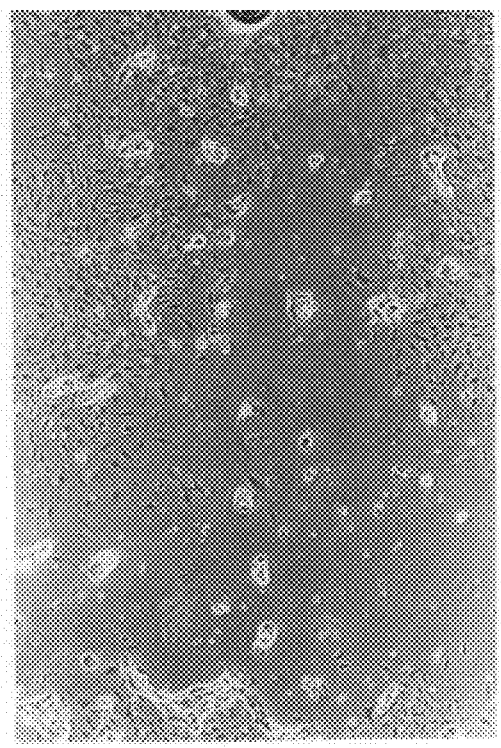
FIGS. 10A and 10B are photomicrographs of a case similar to that shown in FIGS. 7A and 7B, in which L-ascorbic acid 2-phosphate is removed.
Figure 10B:
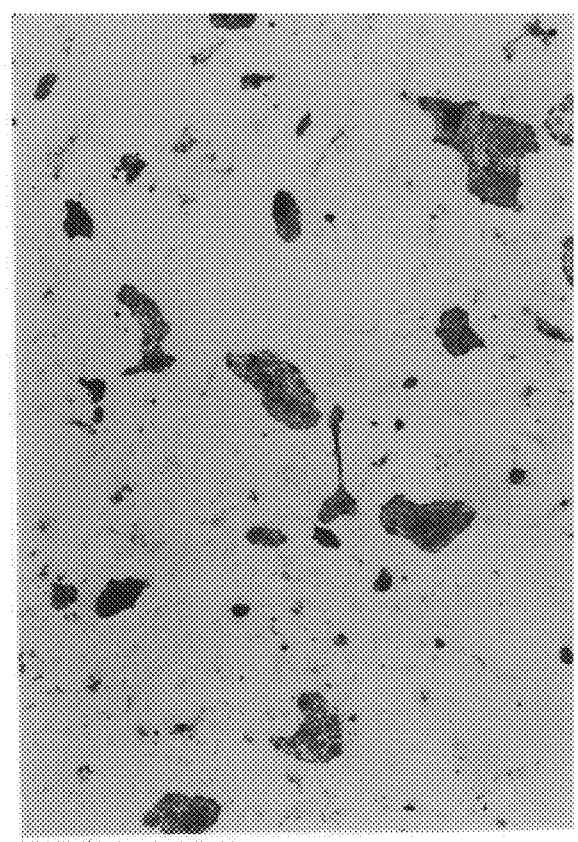
Figure 11A:
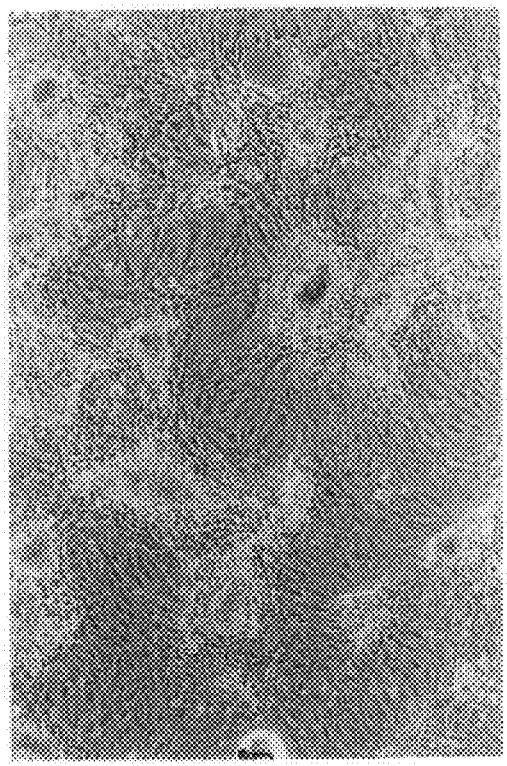
FIGS. 11A and 11B are photomicrographs of a case similar to that shown in FIGS. 7A and 7B, in which DMSO is removed.
Figure 11B:
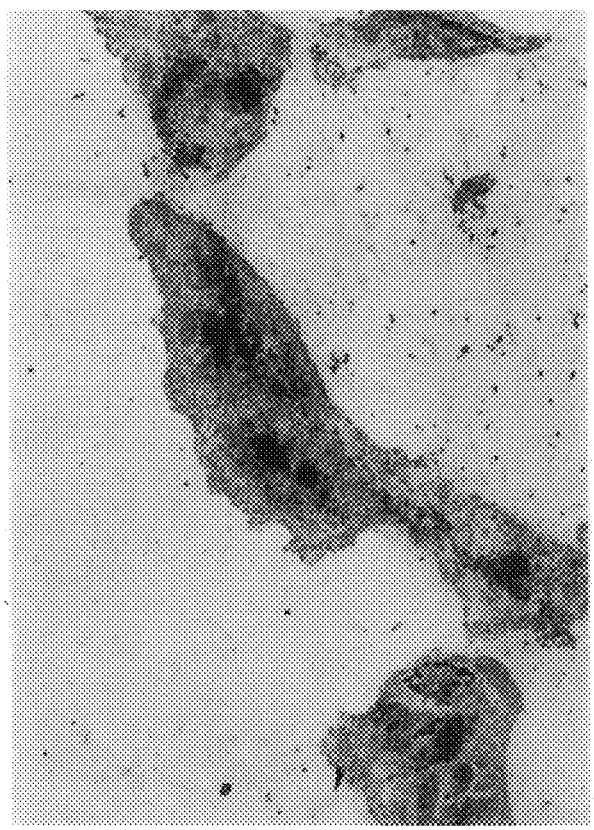

FIG. 7 (control), FIG. 8 (without EGF) FIG. 9 (without nicotinamide) FIG. 10 (without L-ascorbic acid-phosphate) and FIG. 11 (without DMSO) illustrate the effects of these additive factors on hepatocytes and liver parenchymal cells, in the form of phase-contrast figures (×29.4) on the 15th day of subculture and transferrin-stained figures (red) (×30) on the 22nd day of subculture.

FIG. 12 shows the effects of these additive factors as changes with time in the area of hepatocyte clusters, with that on the first day of subculture as 100%.

Figure 13:
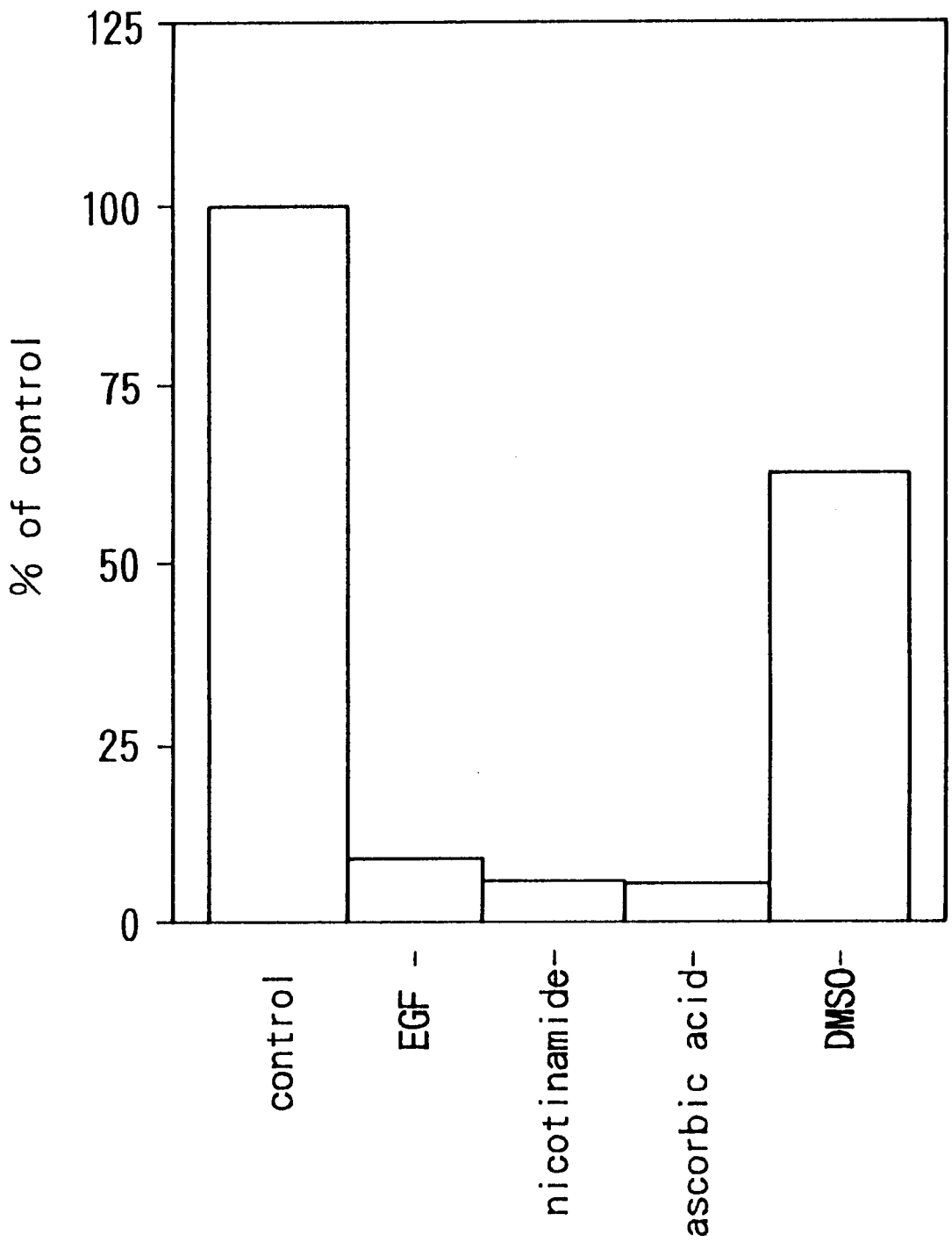
FIG. 13 illustrates the area occupied by anti-transferrin positive cells on the 22nd day of subculture when removing EGF, nicotinamide, L-ascorbic acid 2-phosphate and DMSO, respectively.

Similarly, FIG. 13 demonstrates the effects of the individual additive factors by means of the area of anti-transferrin positive cells on the 22nd day of subculture, with that for the control as 100%.

As is evident from these drawings, inhibition of growth of hepatocytes after subculture was observed in all the systems removing any of EGF, nicotinamide, and L-ascorbic acid-2-phosphate. In the system removing EGF, inhibition of growth of non-parenchymal cells was observed, whereas acceleration of growth of non-parenchymal cells was observed in the system not containing nicotinamide. In the system removing DMSO, growth of non-parenchymal cells was earliest: the hepatocyte clusters began to peel off from the dish on the 22nd days. In all the systems, the hepatocytes were transferrin-positive. In the system not containing FBS, remarkable inhibition of growth of hepatocytes and non-parenchymal cells was observed.

As is clear from these results, the hepatocytes detached in the state of clusters and could adhere to the dish and grow in a system formed by adding FBS, EGF, nicotinamide, L-ascorbic acid-phosphate and DMEM to DMEM and treating these cells with 0.02% EDTA in a confluent state.

Because the dish was not coated with collagen, the hepatocytes could be detached with 0.02% EDTA. By treating with 0.02% EDTA and 0.25% trypsin, the hepatocytes detached in the form of single cells, adhering to the dish, and incorporation of many BrdU was observed. On the seventh day, some hepatocytes died, and thereafter, the status of growth and maintenance of the remaining hepatocytes was poorer then with 0.02% EDTA.

EGF, which had functions of accelerating growth of the hepatocytes and non-parenchymal cells and causing the hepatocytes after subculture to survive, and nicotinamide, which had a function of accelerating growth of "committed progenitor cells," were both essential for the subject system.

L-ascorbic acid-phosphate, which had functions of accelerating growth of the hepatocytes and causing the hepatocytes after subculture to survive, was essential in the system. Various effects of L-ascorbic acid-2-phosphate on hepatocytes and fibroblasts have been reported, and it is considered to have contributed in the system of the present invention to interaction between non-parenchymal and hepatocytes and three-dimensional structure.

DMSO has a function of inhibiting growth of non-parenchymal cells.

In the system of the present invention, "committed progenitor cells" could selectively be cultured by subculturing hepatocytes under conditions permitting growth of hepatic "committed progenitor cells."

Example 2

Hepatic cells having a clonal growth ability of the present invention were obtained as follows.

(1) Culture of Hepatocytes

Cells of liver were sampled from F344 male rats of ages ranging from 4 to 22 weeks by the collagenase perfusion method and centrifuged at a speed (50 g, 1 minute×3). The resultant supernatant was further centrifuged at a speed (150 g, 5 minutes×3), thereby obtaining a non-parenchymal cell fraction as precipitate. These cells were inoculated at $9\times10^5$ cells per culture dishes having a diameter of 3.5 cm and cultured at 37° C. with 5% $CO_2$ for two to three hours in a DMEM medium (containing 10% FBS, 44 mM NaHCO3, 20 mM HEPES, 0.5 mg/l insulin, $10^{-7}$ dexamethasone, 30 mg/l L-proline, penicillin and streptomycin). Then, the medium was replaced with a DMEM medium formed by adding 10 mM nicotinamide, 10 ng/ml EGF and 0.2 mM L-ascorbic acid phosphate to the above-mentioned medium, and another medium further added with 1% DMSO was used on the fourth and subsequent days to continue culture.

(2) Procedures

BrdU was incorporated and photographs of the same fields were taken periodically under a phase contrast microscope to measure the area of the hepatocyte region as indicators of the growth of hepatocytes.

Identification of functional expression of the hepatocytes and non-parenchymal cells was accomplished by an immunocytochemical technique or an enzyme-cytochemical technique using antibodies (OC2, OC3) of ovall cells obtained by Hixson as described above, bile duct cell-markers (BD1: obtained by Hixson as presented above; cytochalasin 7), hepatocyte-markers (antibody against albumin, $\alpha_1$-antitrypsin and transferrin), neoplastic hepatocyte- or immature hepatocyte-markers (antibodies against GST-P, α-fetoprotein, γ-GTP stain), and stellate cell-markers (antibody of desmin). Organelles were observed in detail with a transmission electron microscope.

To compare differences in the results of culture between ages in weeks of rats from which hepatic cells were sampled, samples on the tenth day of culture was HE-stained, and the forming ability of hepatocyte colonies was measured under a microscope. Collections each having 8 or more cells were counted as colonies.

Culture was conducted in systems removing each of such additive factors from the medium as FBS, nicotinamide, EGF, L-ascorbic acid phosphate and DMSO to investigate the effects of the individual additive factors on hepatocyte colonies and non-parenchyma cells.

(3) Results

Figure 14:
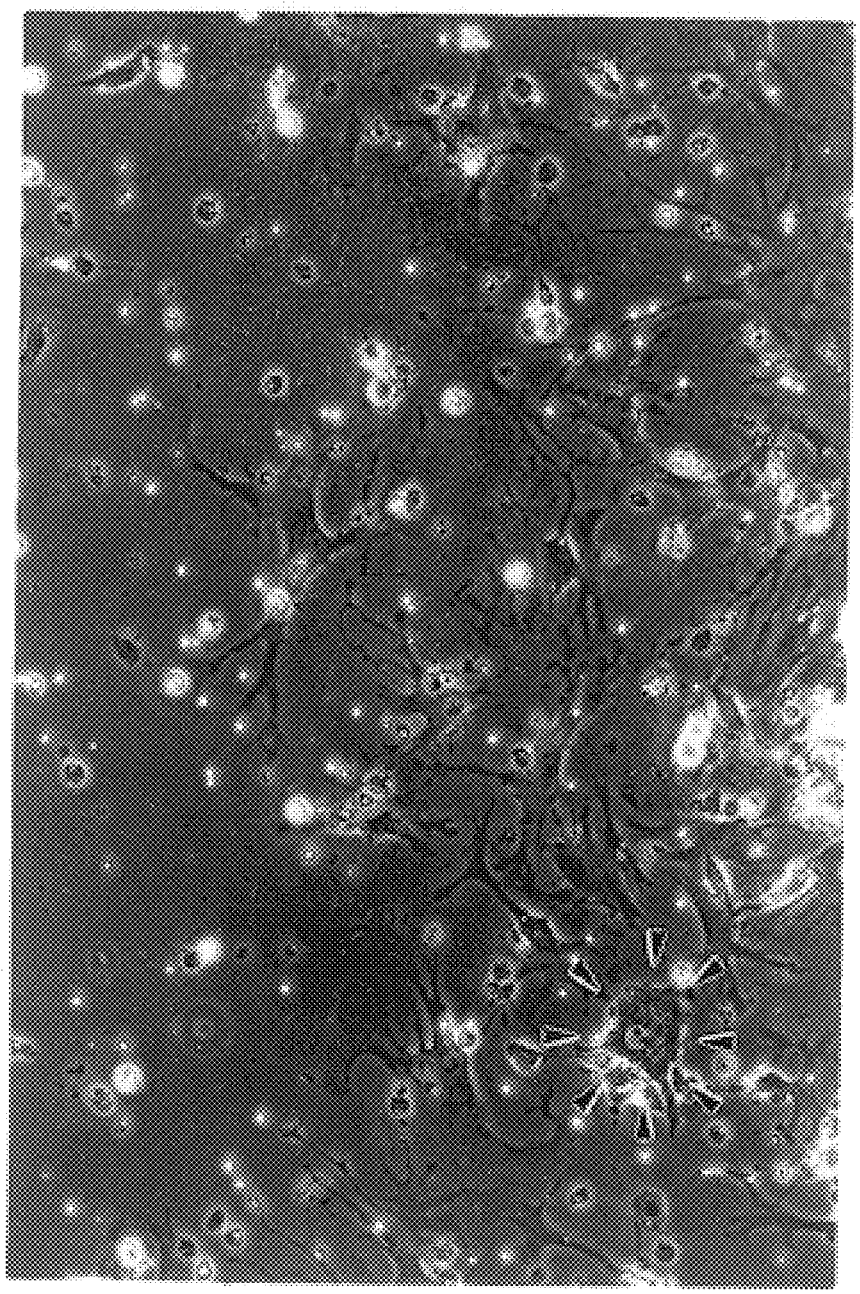
FIG. 14 is a phase contrast photomicrograph (147 magnifications) illustrating the state on the third day of culture of cells sampled from a rat having an age of eight weeks.
Figure 15:
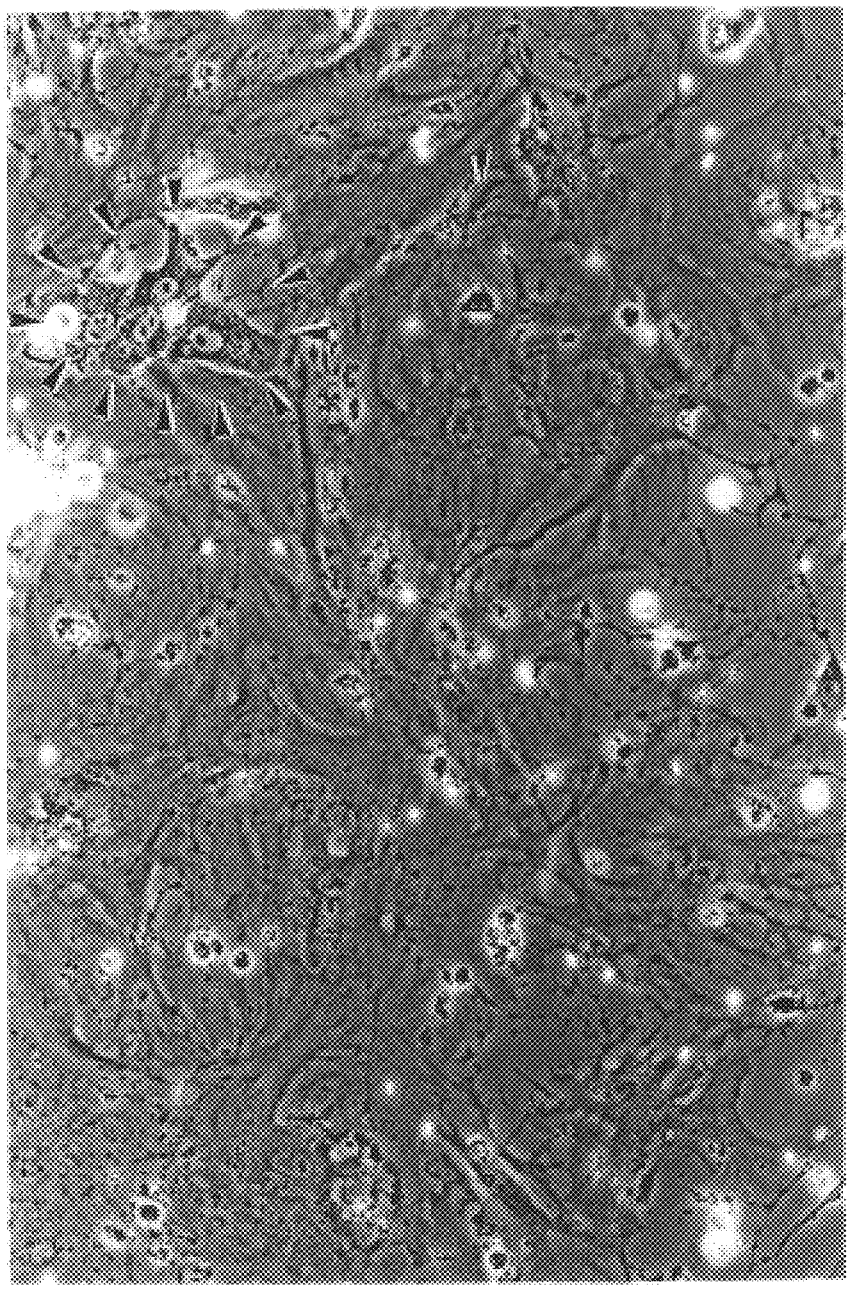
FIG. 15 is a phase contrast photomicrograph illustrating the state of the same cell as that shown in FIG. 14 on the fifth day of culture within the same field of view.
Figure 16:
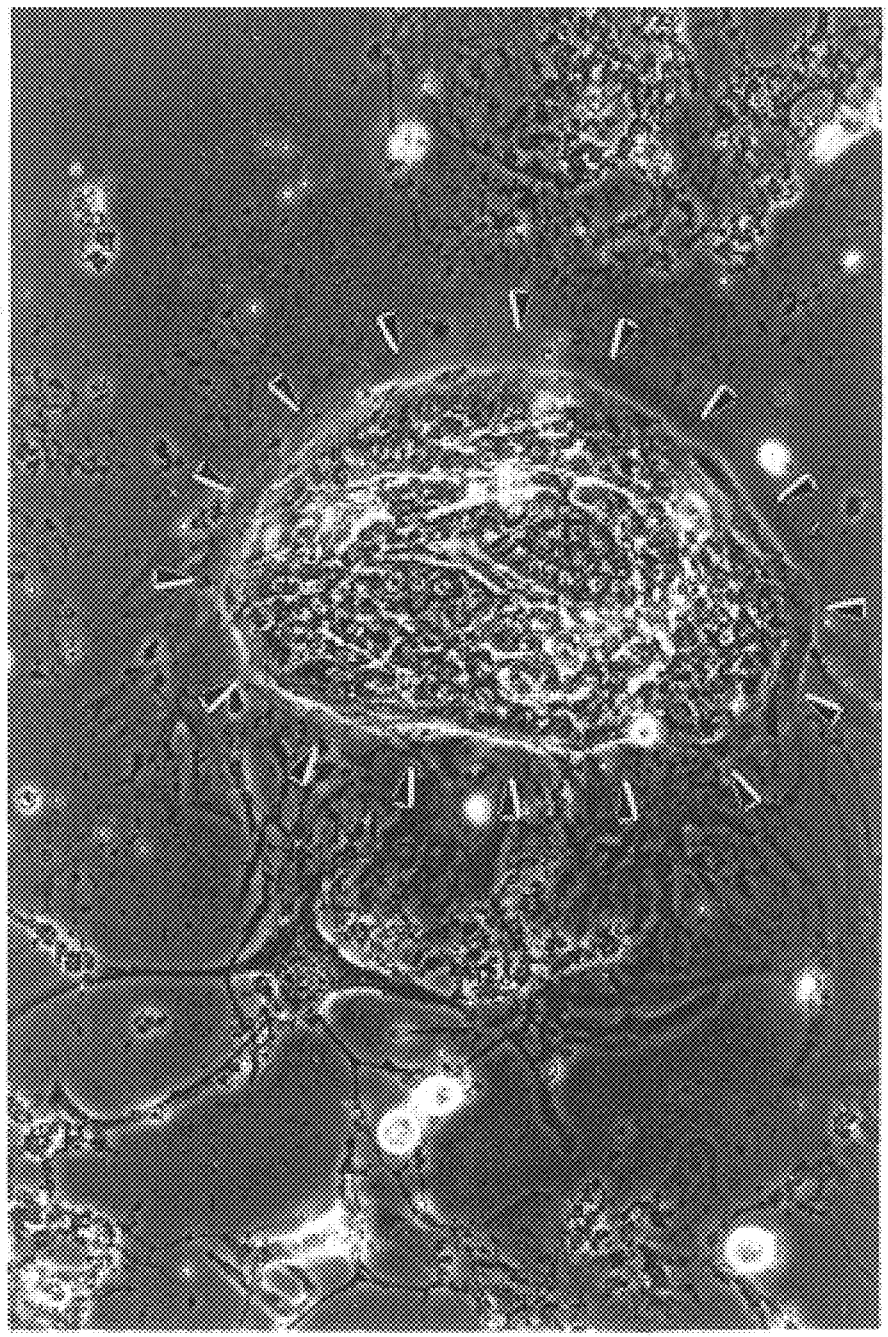
FIG. 16 is a phase contrast photomicrograph illustrating the state of the same cell as that shown in FIG. 14 on the 15th day of culture within the same field of view.

As a result of culture under the conditions shown in (1) above, small hepatocytes were observed to form colonies and clonally grow, as shown in phase-contrast photomicrographs in FIGS. 14 to 16. These FIGS. 14 to 16 are phase contrast figures (147 magnifications) of the same field of view of cell culture sampled from rats having an age of eight weeks: a single small hepatic cell on the third day of culture (FIG. 14) grows into four cells on the fifth day (FIG. 15) and into about 300 cells in a colony on the 15th day (FIG. 16).

Figure 17:
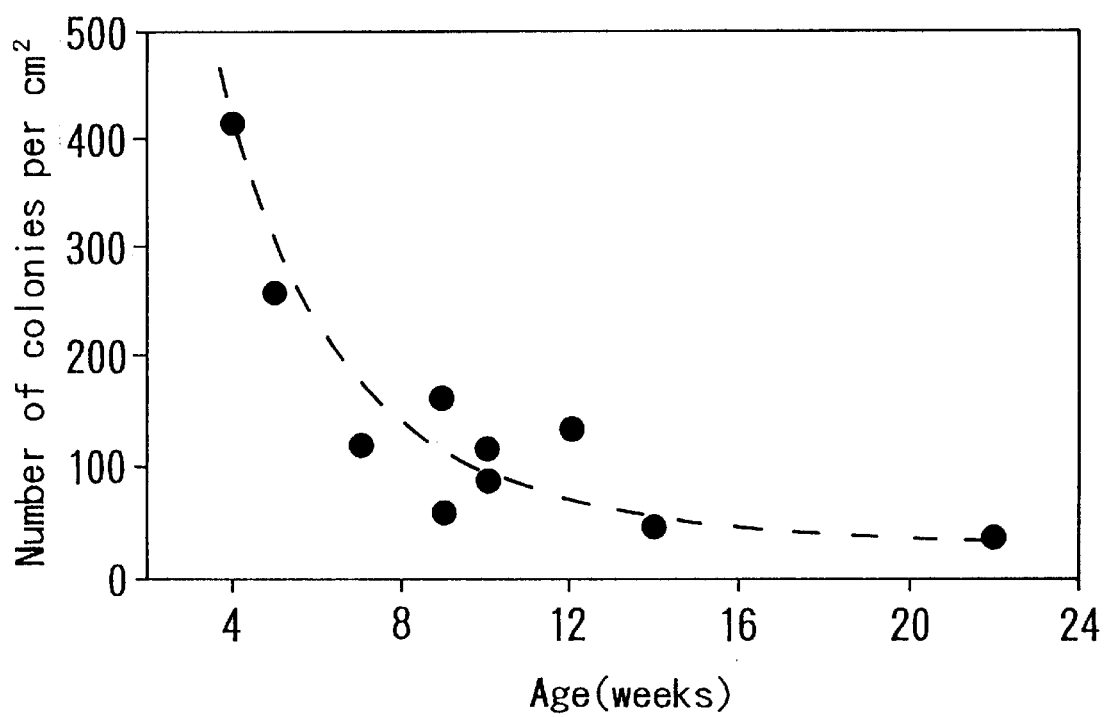
FIG. 17 illustrates the relationship between the age in weeks of the rat from which cells are sampled and the number of hepatocyte colonies per $cm^2$ on the tenth day of culture.
Figure 18:
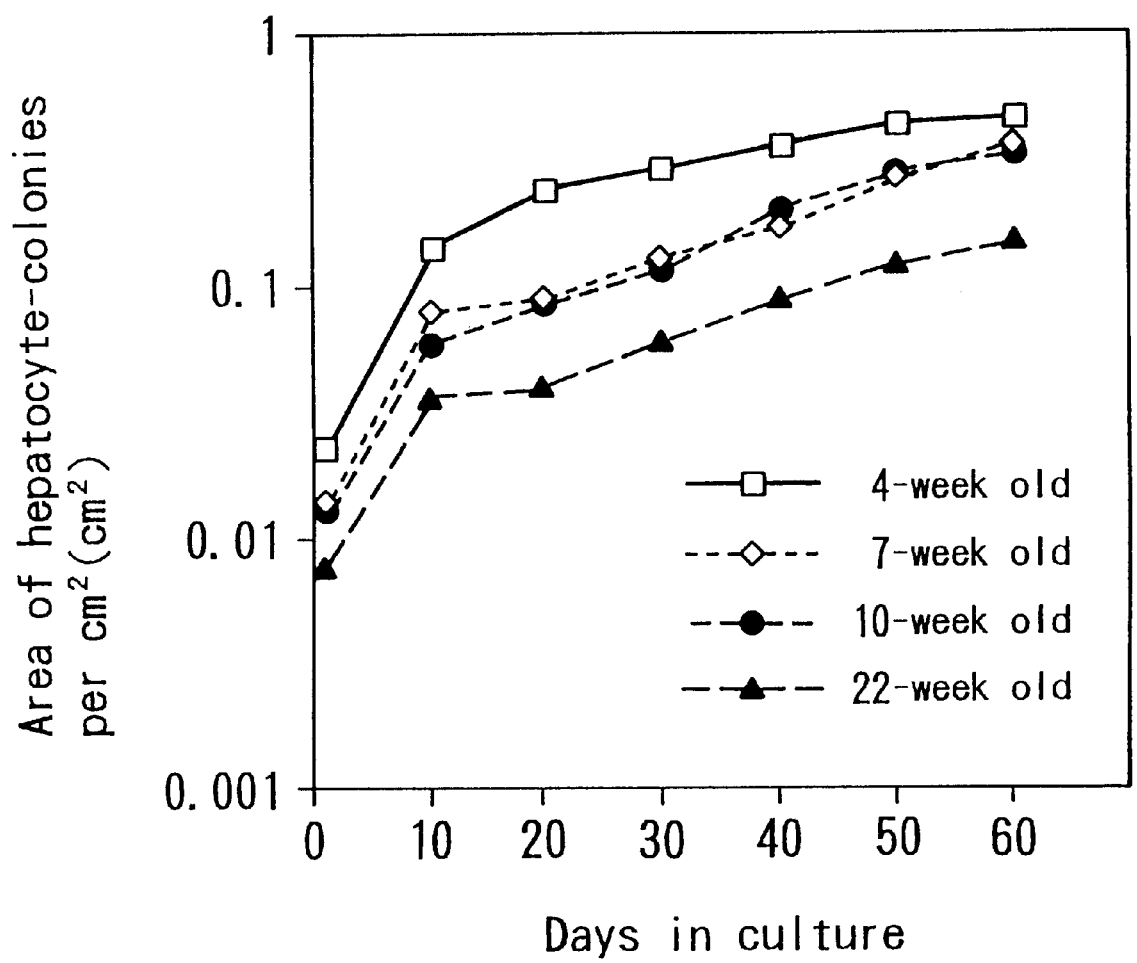
FIG. 18 illustrates the relationship between days in culture and the area of hepatocyte colonies for each age in week of the rats.
Figure 19:
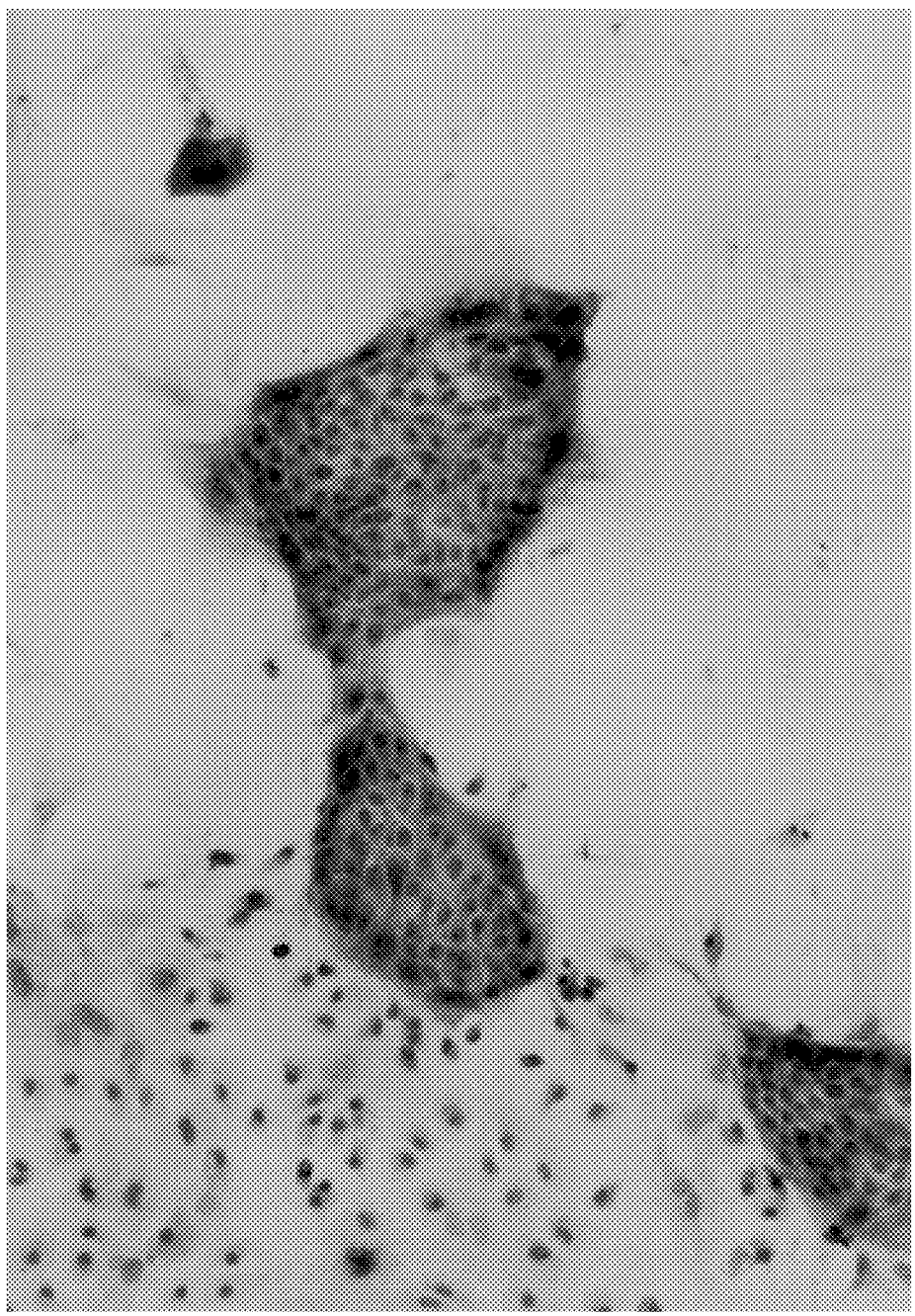
FIG. 19 is a photomicrograph (75.8 magnifications) illustrating an HE staining figure of hepatocyte colonies on the 10th day of culture of cells sampled from a rat having an age of eight weeks.

The colony froming ability decreased as the age in weeks of the rat from which hepatic cells were sampled increased as shown in FIG. 17. Irrespective of the age in weeks of rat, the growth curves were almost identical as shown in FIG. 18. These results suggest that hepatic cells forming colonies are progenitor cells.

Figure 20:
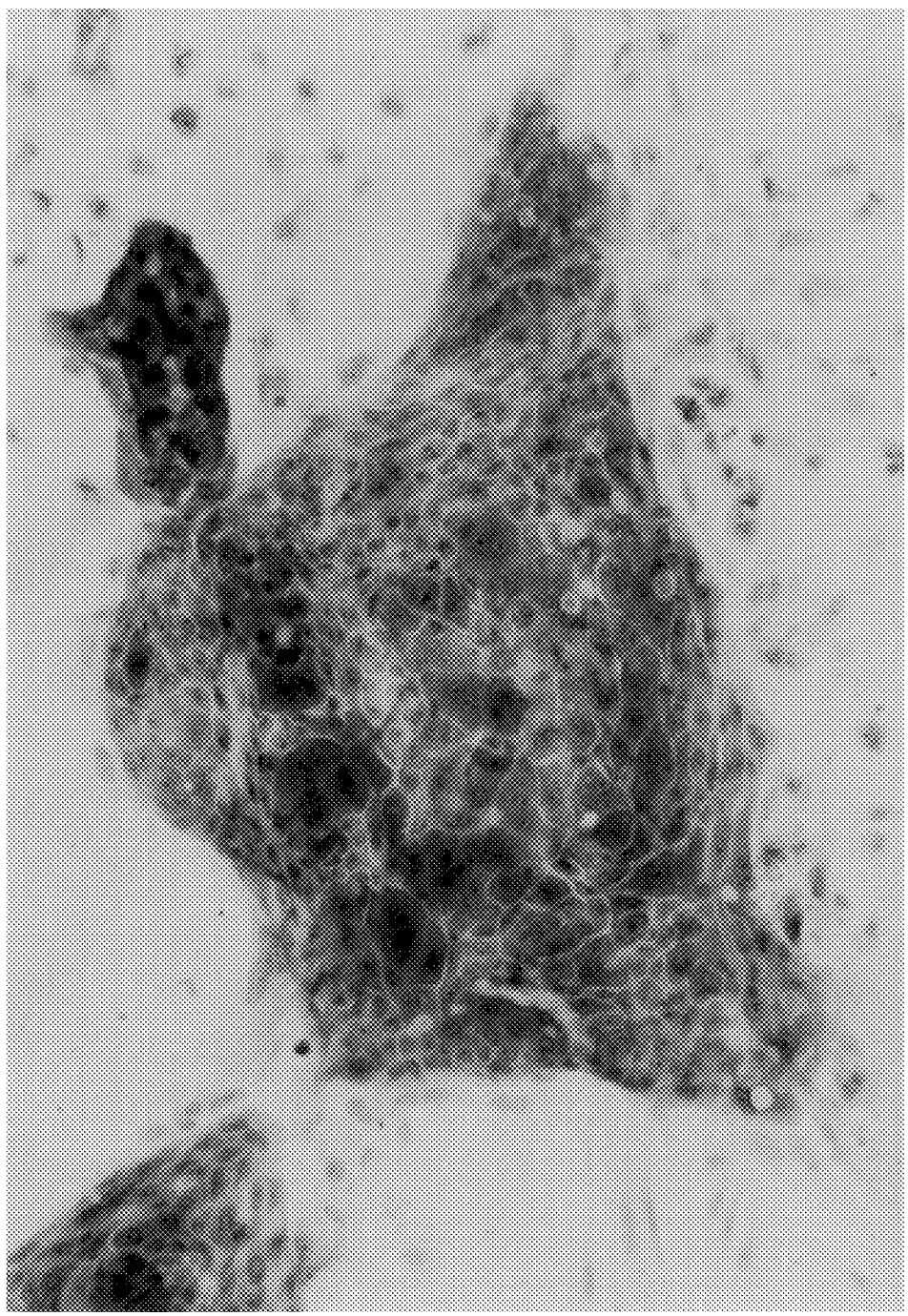
FIG. 20 is a photomicrograph (75.8 magnifications) illustrating HE staining figure of hepatocyte colonies on the 20th day of culture of cells sampled from the same rat as in FIG. 19.
Figure 21:
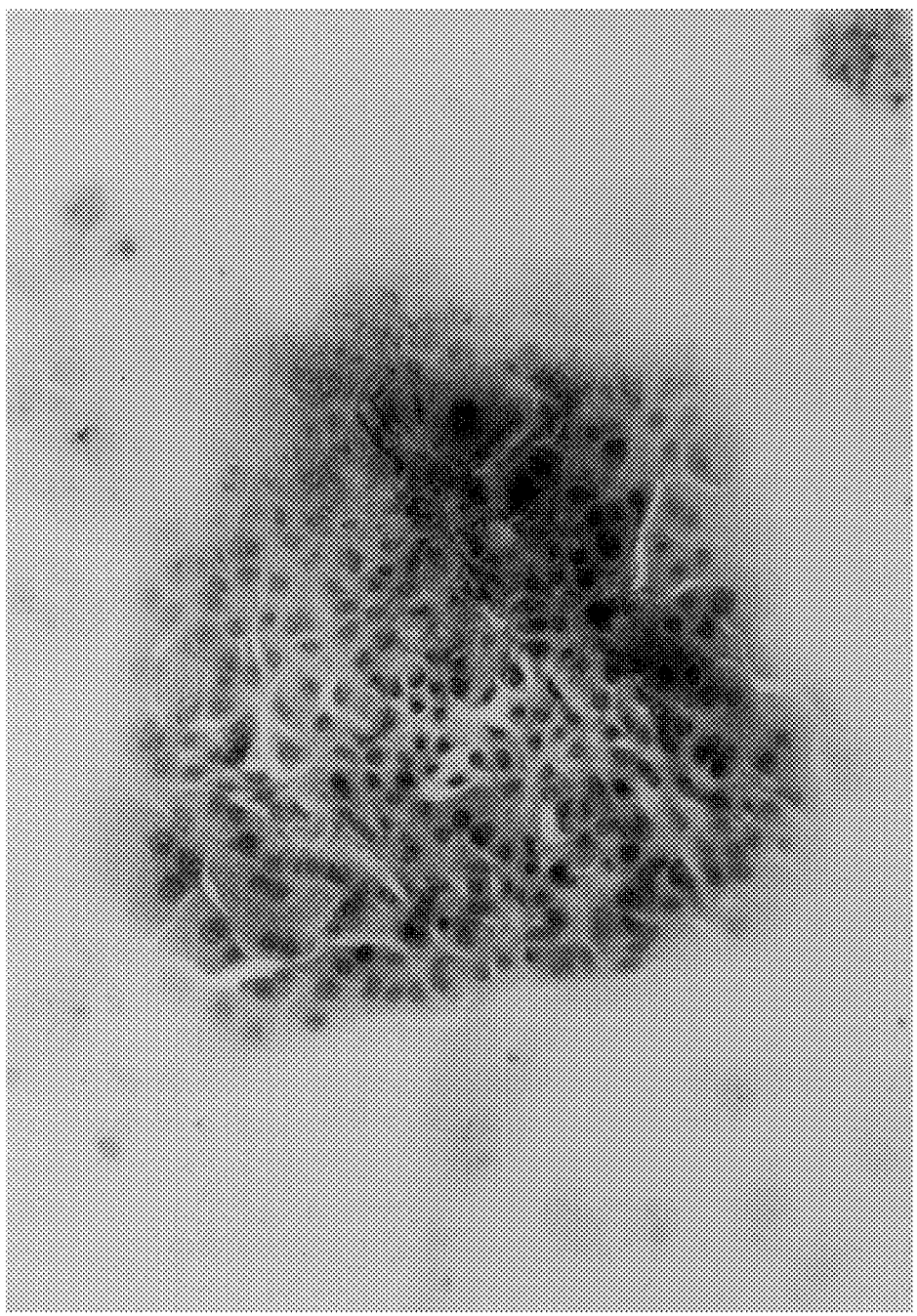
FIG. 21 is a photomicrograph (200 magnifications) illustrating a BDI staining figure of a hepatocyte colony on 30th day of culture of cells sampled from a rat having an age of seven weeks.
Figure 22:
FIG. 22 is a photomicrograph (152 magnifications) illustrating a cytochalasin 7 staining figure of a hepatocyte colony on the 25th day of culture of cells sampled from a rat having an age of eight weeks.

From the result of HE staining, large binuclear cells were observed in colonies and maltilayered structures in peripheral area of colonies on the 20th day of culture (FIG. 20) although the colonies consisted of homogeneous small hepatocytes on the tenth day of culture (FIG. 20). In some portion of colonies, positive cells to bile duct cell-markers, BD1 (FIG. 22) and cytochalasin 7 (FIG. 22) were observed. From these results, cells of colonies are considered to contain progenitor cells of bile duct cells or to be stem cells capable of differentiating into hepatocytes or bile duct cells.

Figure 23:
FIG. 23 is a photomicrograph (606 magnifications) illustrating an albumin staining figure of a hepatocyte colony on the 25th day of culture of cells sampled from a rat having an age of eight weeks.
Figure 24:
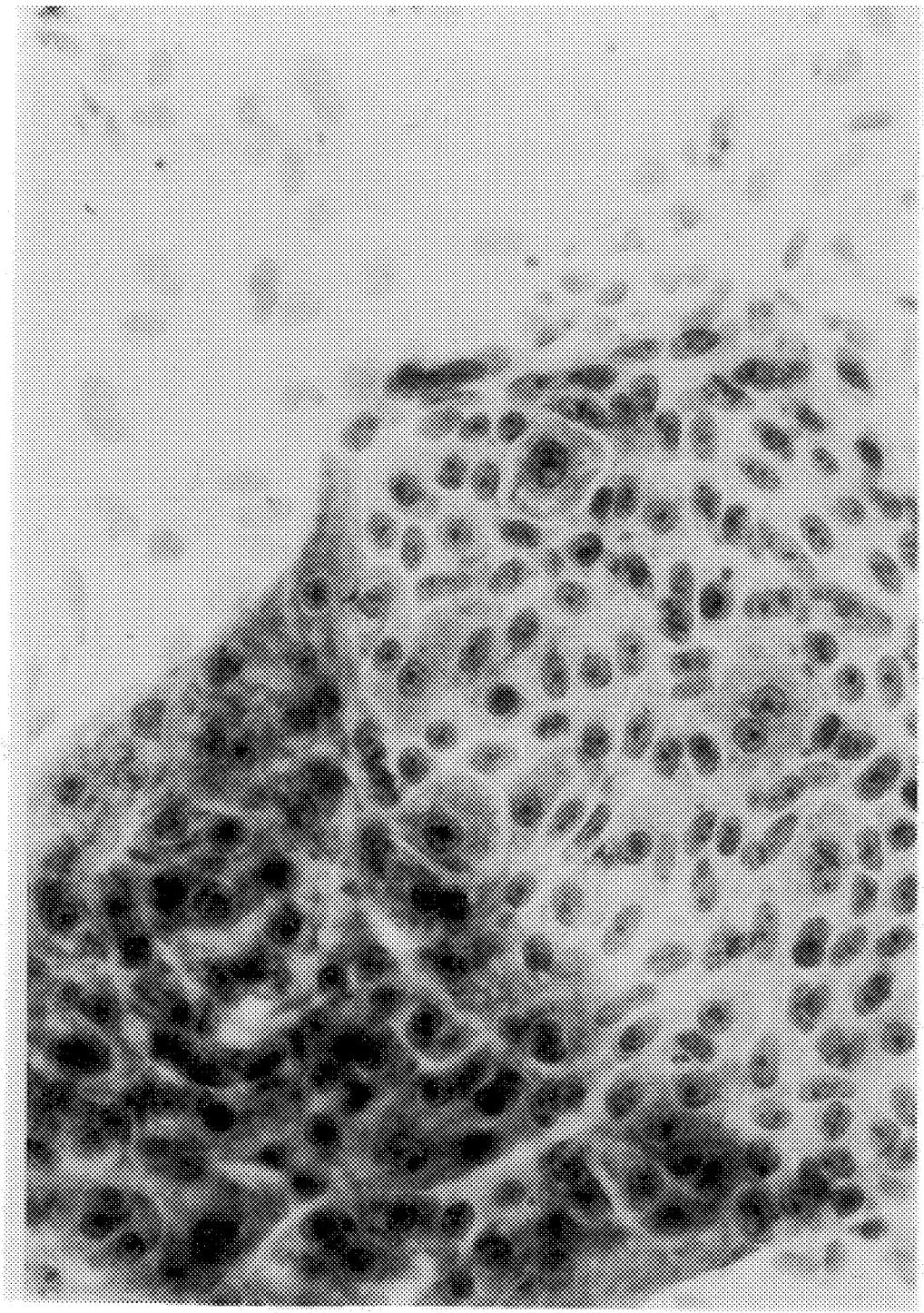
FIG. 24 is a photomicrograph (242 magnifications) illustrating an $α_1$-antitrypsin staining figure of a hepatocyte colony on the 25th day of culture of cells sampled from a rat having an age of eight weeks.
Figure 25:
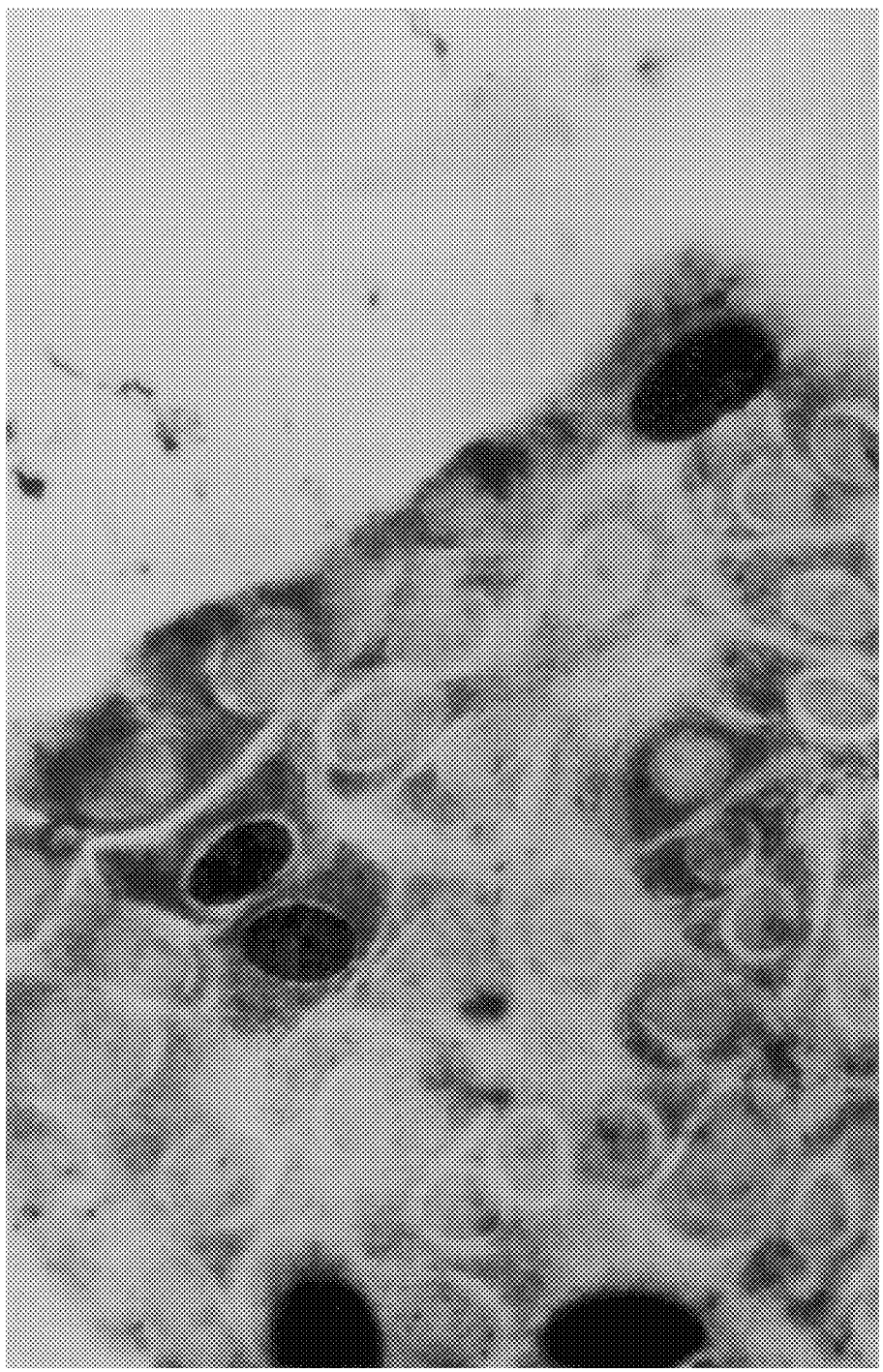
FIG. 25 is a photomicrograph (606 magnifications) illustrating a transferrin BrdU double staining figure of a hepatocyte colony on the 30th day of culture of cells sampled from a rat having an age of seven weeks.
Figure 26:
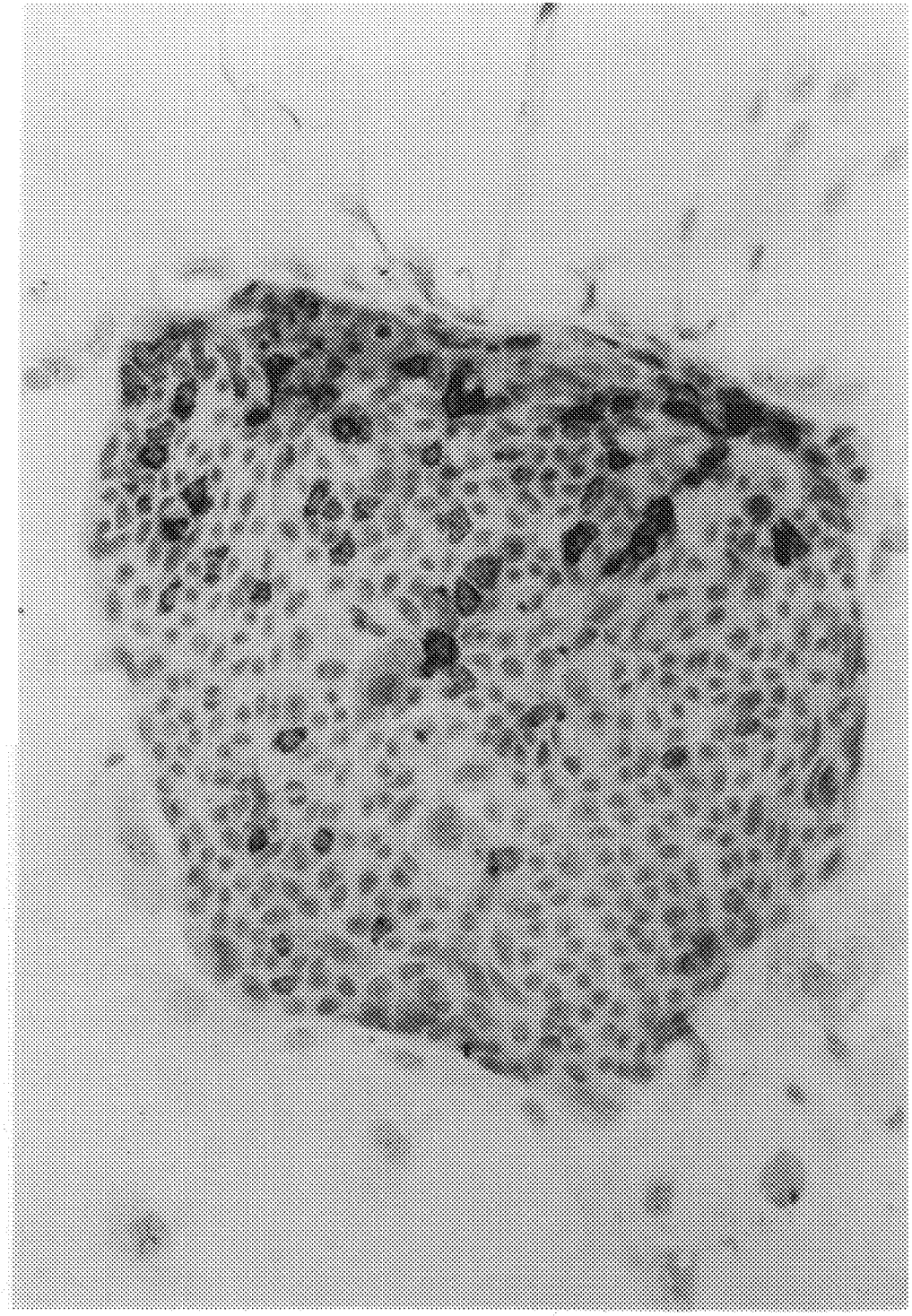
FIG. 26 is a photomicrograph (152 magnifications) illustrating an α-fetoprotein staining figure of a hepatocyte colony on the 30th day of culture of cells sampled from a rat having an age of seven weeks.
Figure 27:
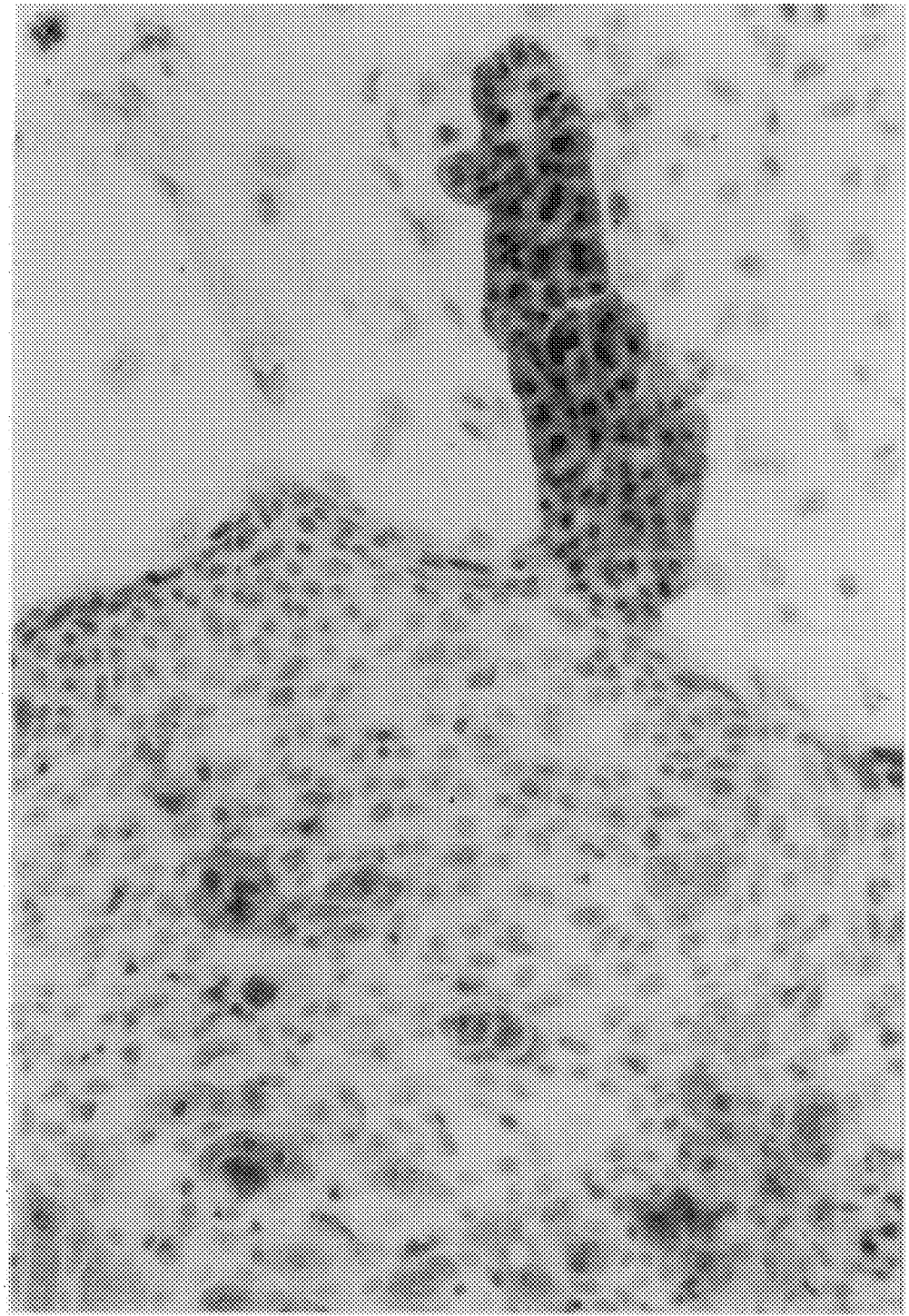
FIG. 27 is a photomicrograph (152 magnifications) illustrating a GST-P staining figure of a hepatocyte colony on the 30th day of culture of cells sampled from a rat having an age of seven weeks.
Figure 28:
FIG. 28 is a photomicrograph (152 magnifications) illustrating a γ-GTP staining figure of a hepatocyte colony on the 30th day of culture of cells sampled from a rat having an age of seven weeks.
Figure 29:
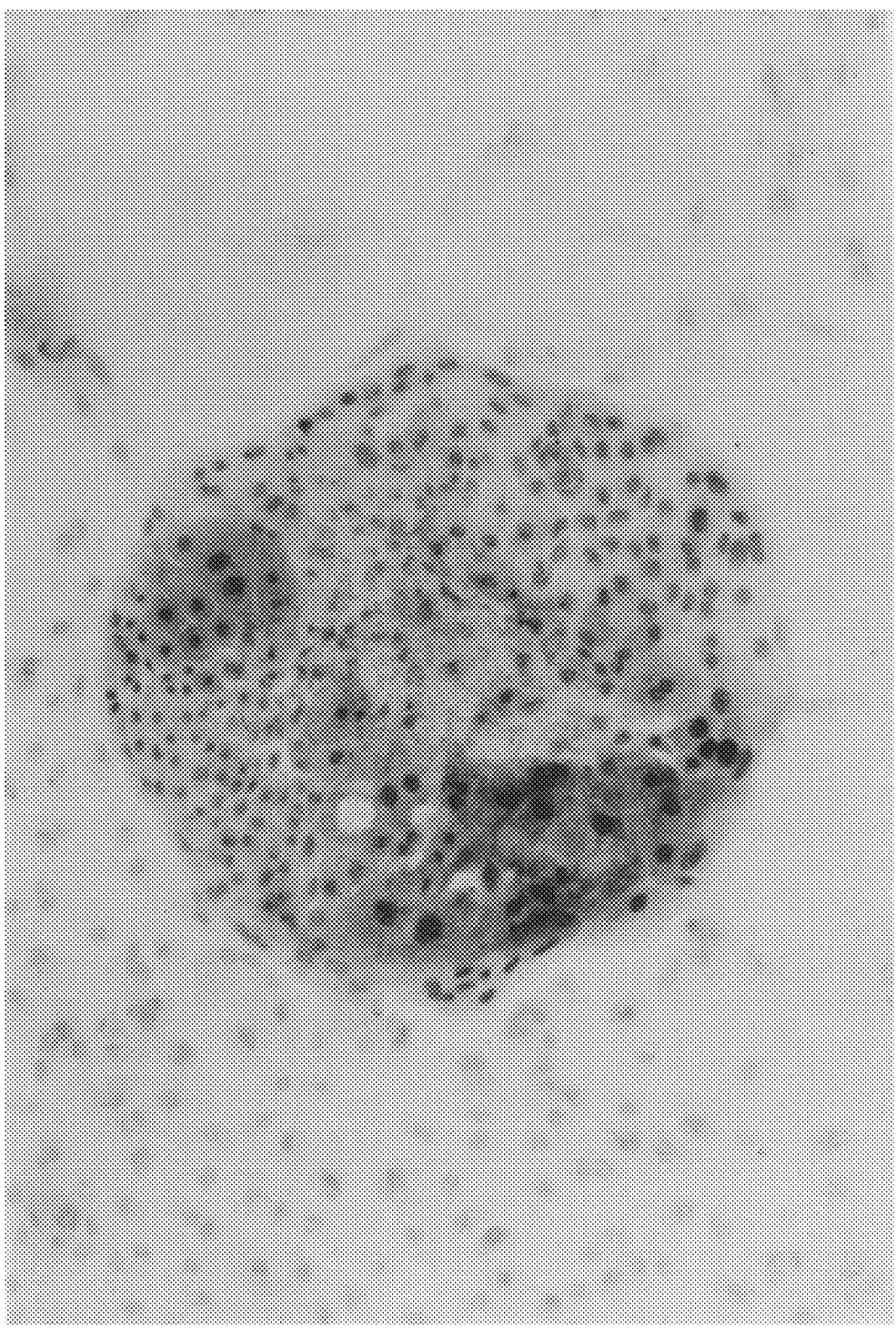
FIG. 29 is a photomicrograph (152 magnifications) illustrating an OC2 staining figure of a hepatocyte colony on the 22nd day of culture of cells sampled from a rat having an age of ten weeks.
Figure 30:
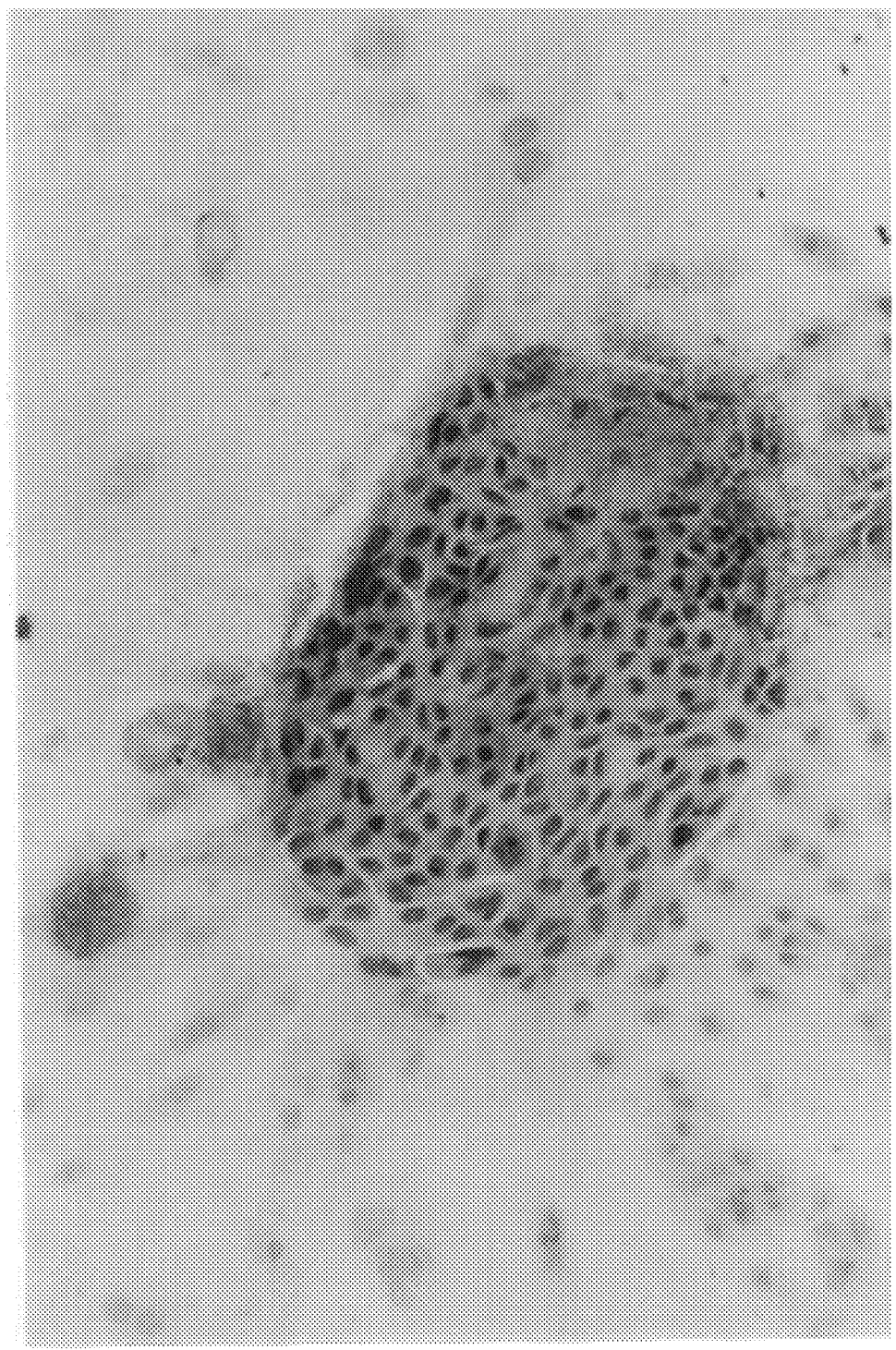
FIG. 30 is a photomicrograph (152 magnifications) illustrating an OC3 staining figure of a hepatocyte colony on the 22nd day of culture of cells sampled from a rat having an age of ten weeks.

Then, these colonies of cells were confirmed to be positive to the hepatocyte-markers, and comprise cells expressing normal functions. More specifically, FIG. 23 is a photomicrograph of albumin-stained colonies, and FIG. 24 is a photomicrograph of $\alpha_1$-antitrypsin-stained colonies. In the results of double staining with transferrin and BrdU, incorporation of BrdU into cells positive to transferrin was observed as shown in FIG. 25. The cells of these colonies were partially positive to neoplastic hepatocyte- or immature hepatocyte-markers (FIG. 26; $\alpha$ fetoprotein stoin; FIG. 27; GST-P stain; and FIG. 28: $\gamma$-GTP stain), and positive to antibodies of ovall cells (FIG. 29: OC2 stain; FIG. 30: OC3 stain).

Figure 31:
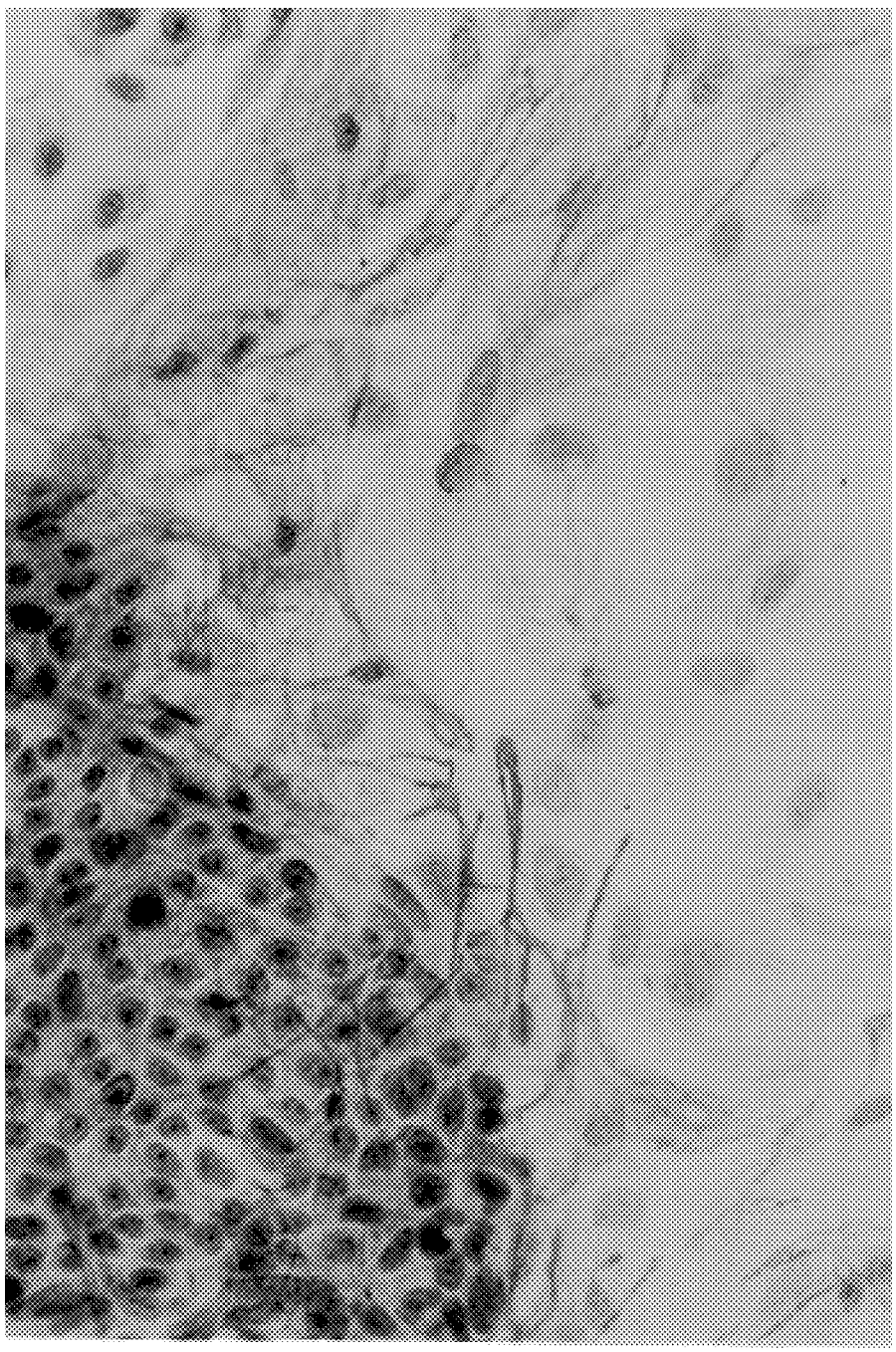
FIG. 31 is a photomicrograph (242 magnifications) illustrating a desmin staining figure of a hepatocyte colony on the 25th day of culture of cells sampled from a rat having an age of eight weeks.

On the other hand, part of non-parenchymal cells around colonies were positive to desmin antibody which was a stellate cell-marker. However because negative cells were also observed (FIG. 31), presence was confirmed of many non-parenchymal cells other than stellate cell around the colonies.

TABLE 2 shows the results of the test on samples removing each of the additive factors from the medium. In this test, culture dishes on the 31st day of culture were stained with albumin, the number of hepatocyte colonies per $cm^2$ was counted with a mass containing eight or more cells positive to albumin counted as one colony. The average of the thus counted numbers of colonies (n=3) is shown in TABLE 2. Phase contrast photomicrographs of colonies for the system containing all the additive factors and the systems removing each of the additive factors are shown in FIGS. 32 to 37.

TABLE 2

| Medium | Number of hepatic cell colonies (average ± SD) | Non-parenchymal cell |
|---|---|---|
| Control | 67.5 ± 6.4 | + |
| EGF(−) | 16.8 ± 8.1 | + |
| Nicotinamide(−) | 66.6 ± 1.9 | ++ |
| L-ascorbic acid phosphate(−) | 1.0 ± 1.9 | ++ |
| DMSO(−) | 24.8 ± 4.8 | ++ |
| FBS(−) | 0 | − |

Figure 32:
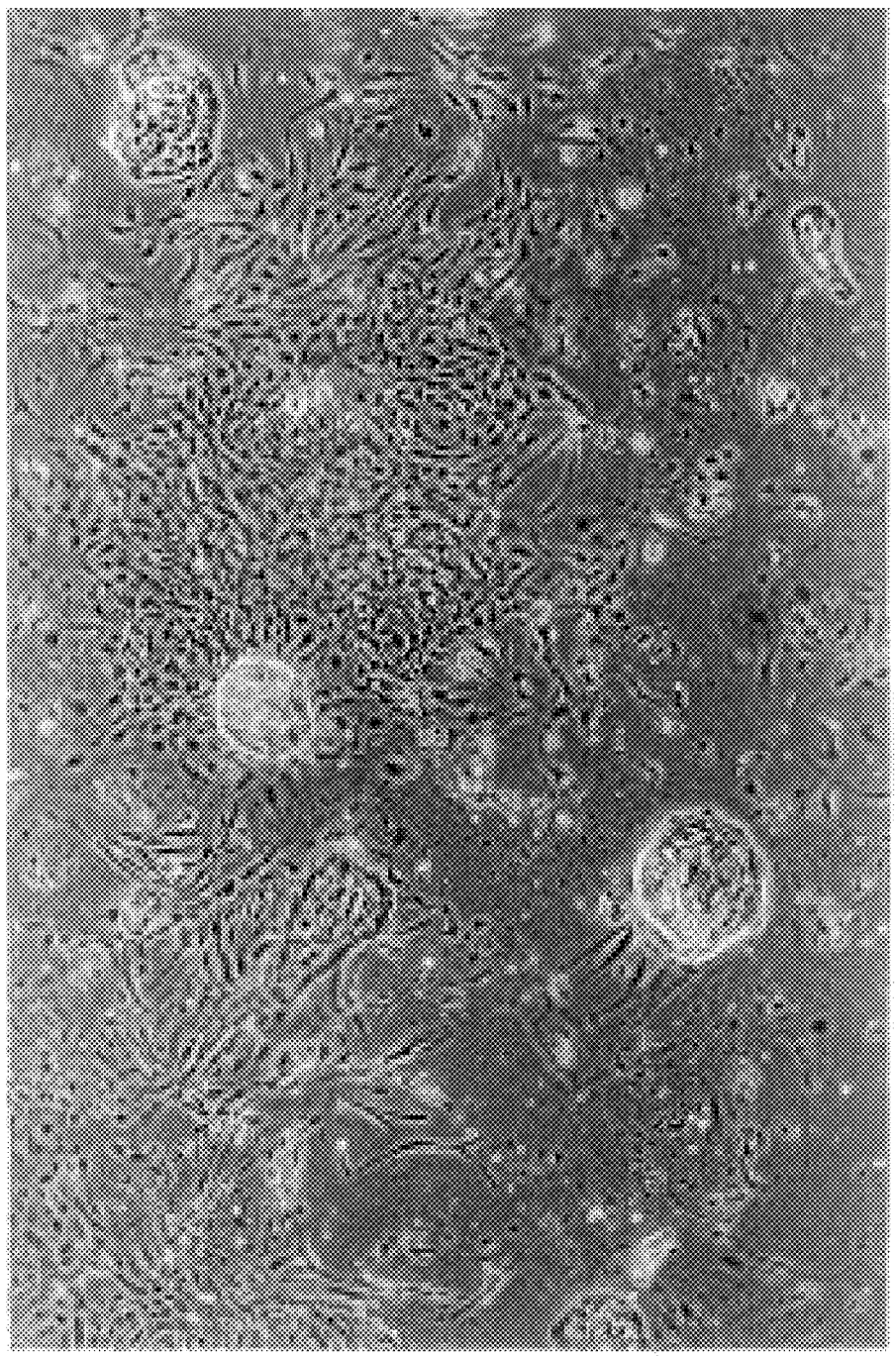
FIG. 32 is a photomicrograph (29.4 magnifications) illustrating a phase contrast figure of hepatocyte colonies on the 31st day of culture of cells sampled from a rat having an age of eight weeks, as cultured in a system (control) added with all the additive factors into the medium.
Figure 33:
FIG. 33 is a phase contrast photomicrograph illustrating the effect on hepatocytes and non-parenchymal cells when removing EGP corresponding to FIG. 32.
Figure 34:
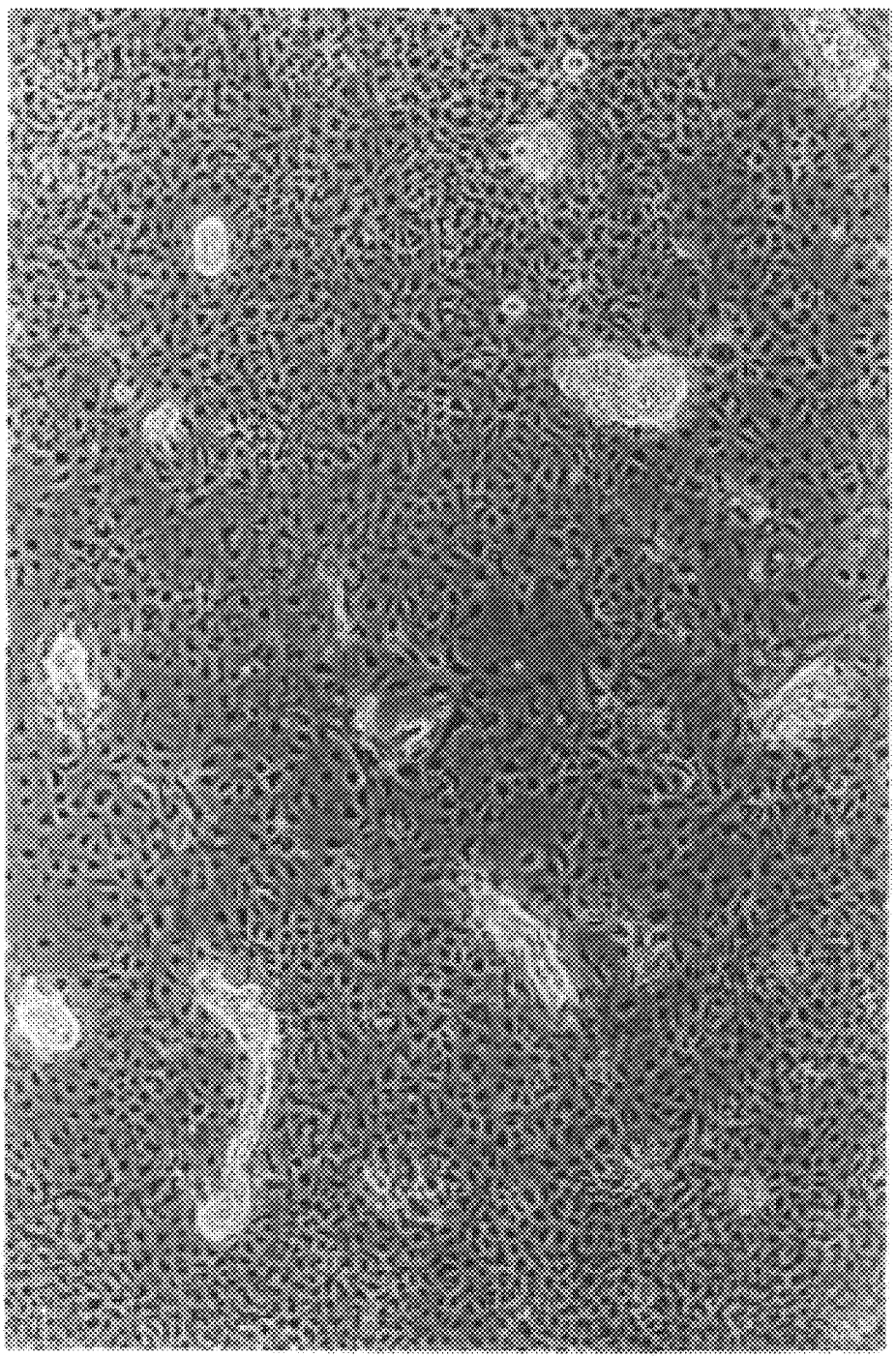
FIG. 34 is a phase contrast photomicrograph illustrating the effect on hepatocytes and non-parenchymal cells when removing nicotinamide corresponding to FIG. 32.
Figure 35:
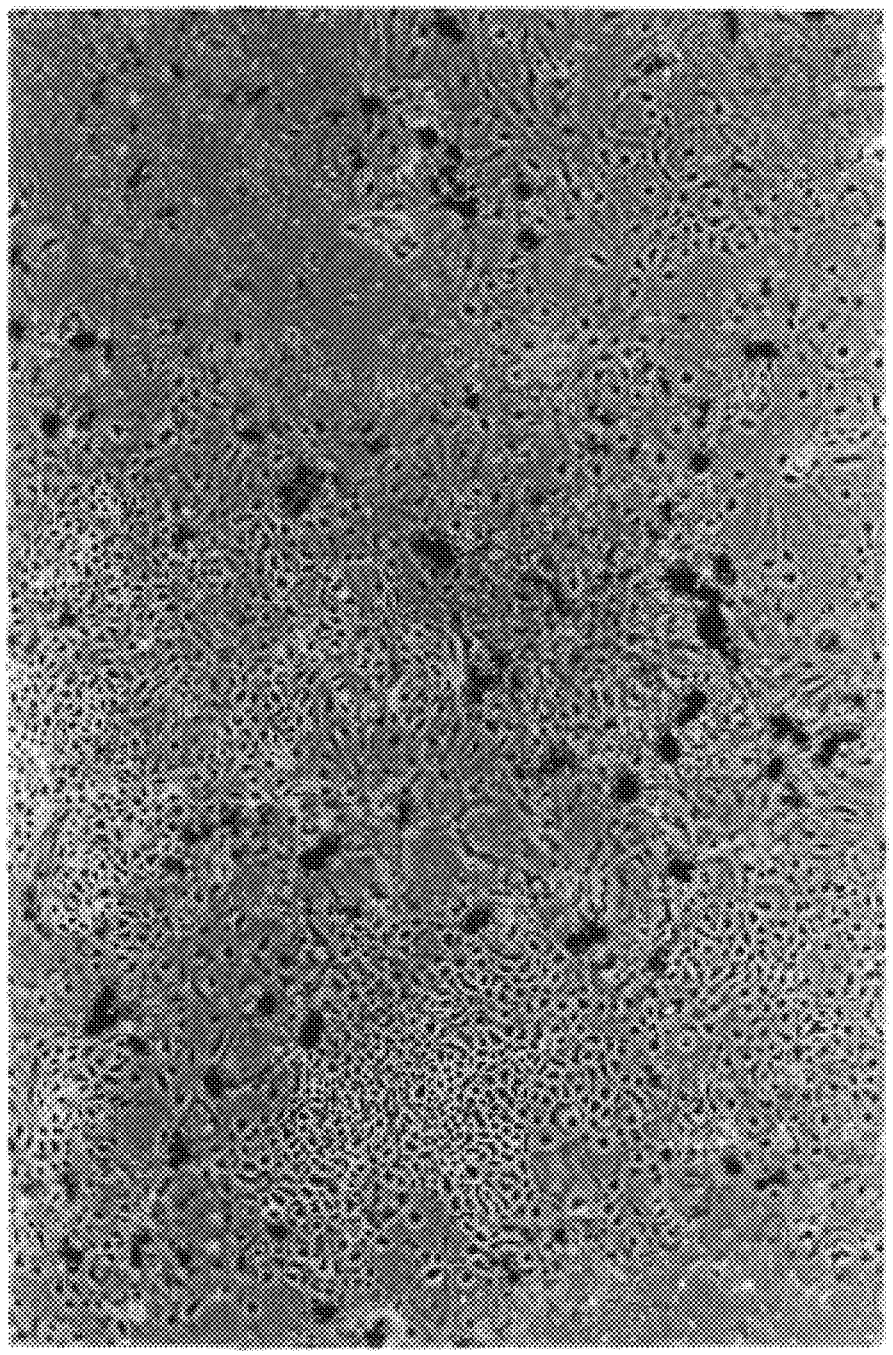
FIG. 35 is a phase contrast photomicrograph illustrating the effect on hepatocytes and non-parenchymal cells when removing L-ascorbic acid phosphate corresponding to FIG. 32.
Figure 36:
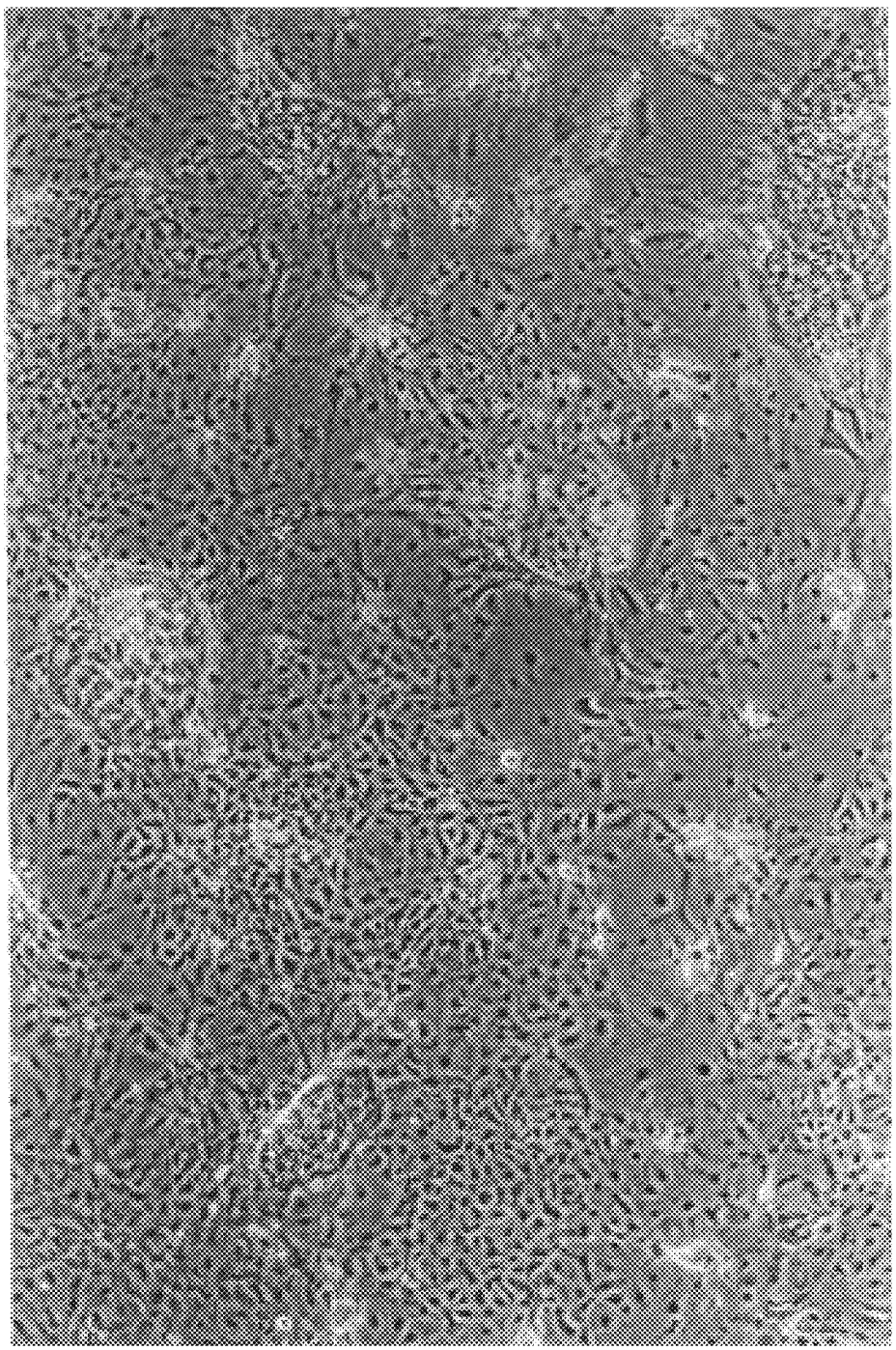
FIG. 36 is a phase contrast photomicrograph illustrating the effect on hepatocytes and non-parenchymal cells when removing DMSO corresponding to FIG. 32.
Figure 37:
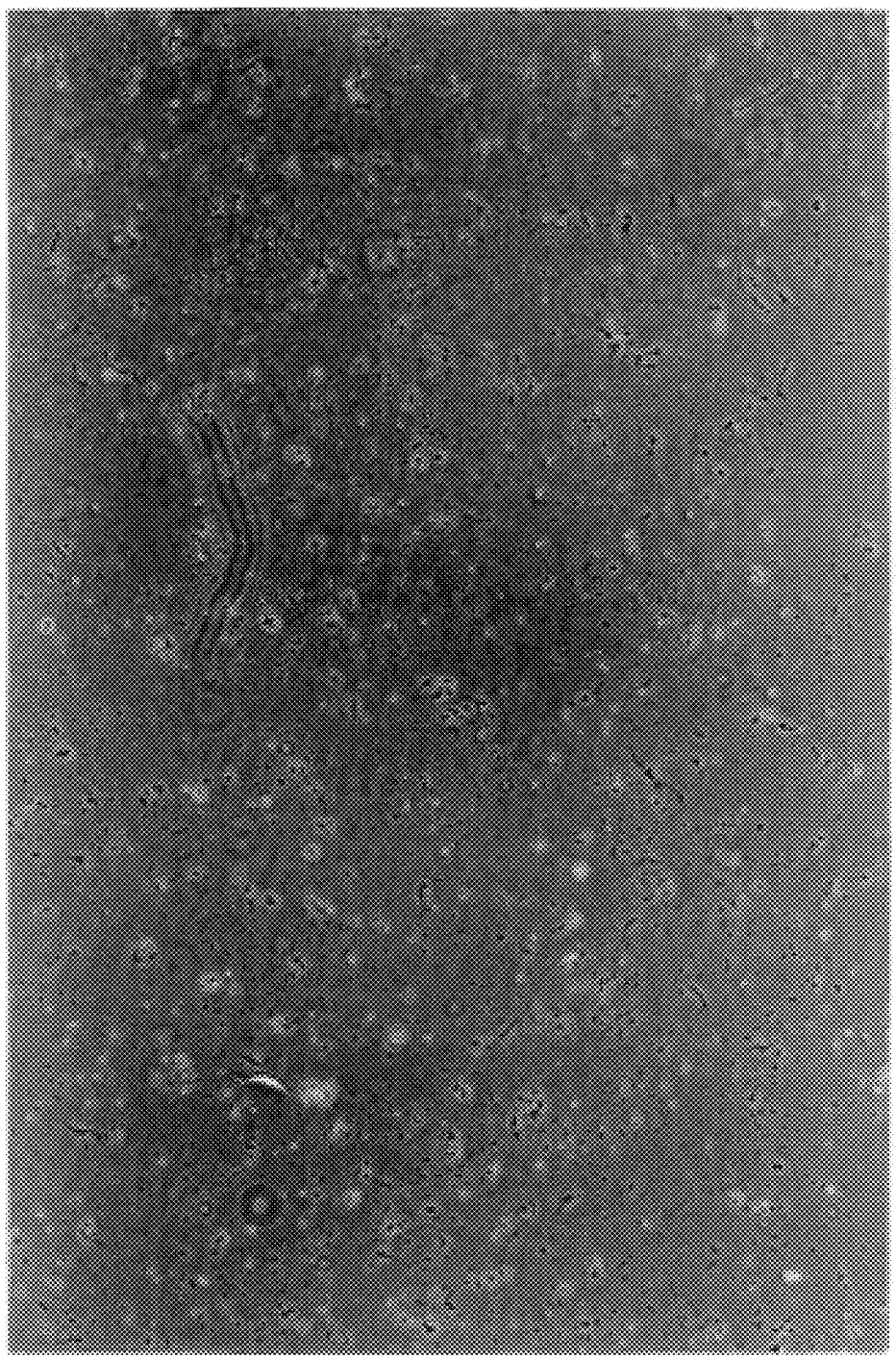
FIG. 37 is a phase contrast photomicrograph illustrating the effect on hepatocytes and non-parenchymal cells when removing FBS corresponding to FIG. 32.

As is clear from TABLE 2, there was no difference in growth of non-parenchymal cells as compared with the control in the system removing EGF in which formation of hepatocyte colonies was apparently inhibited (see FIGS. 32 and 33). In the nicotinamide (−) system, on the other hand, while growth of non-parenchymal cells was accelerated, the forming ability of hepatocyte colonies was not affected. In this nicotinamide (−) system, however, the hepatic cells exhibited a large in size, a hepatic cord-like structure, and form expressing the highly differentiated character of hepatocytes at compared with the control (FIG. 34). In the L-ascorbic acid phosphate (−) system, growth or non-parenchymal cells was accelerated, whereas almost no hepatocyte colonies were formed (FIG. 35). In the DMSO (−) system, growth of non-parenchymal cells was accelerated, but the forming ability of hepatocyte colonies was low as compared with the control (FIG. 36). In the FBS (−) system, both non-parenchymal and hepatocytes would not continue to live (FIG. 37).

These results permitted confirmation that, in order to obtain liver paranchymal cells of the present invention, addition of FBS and ascorbic acid to the culture medium is essential EGF and DMSO, not essential for forming hepatocyte colonies, have a function of accelerating formation of hepatocyte colonies, and nicotinamide is a factor having a relationship with differentiation of hepatocytes. Nicotinamide, ascorbic acid and DMSO were recognized to have a function of inhibiting growth of non-parenchymal cells.

Figure 38A:
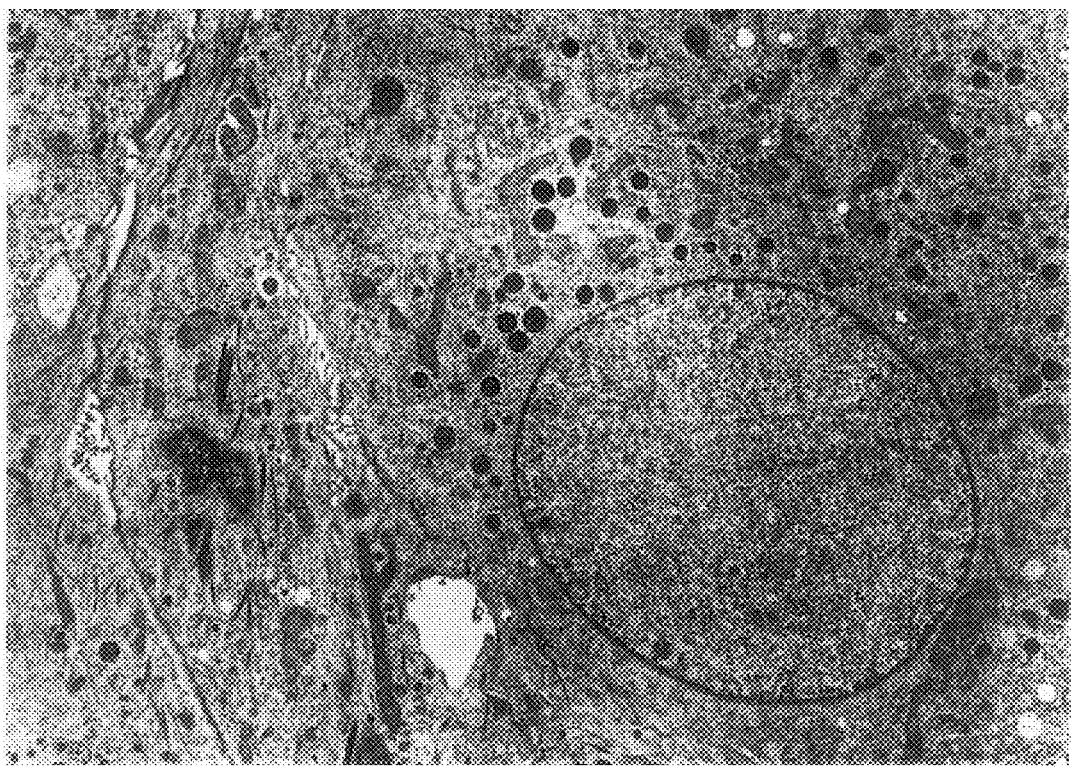
FIG. 38A and 38B are transmission electron microscopic photomicrographs (d: 4,250 magnifications, b: 21,300 magnifications) of a hepatocyte colony on the tenth day of culture of cells sampled from a rat having an age of eight weeks.
Figure 38B:
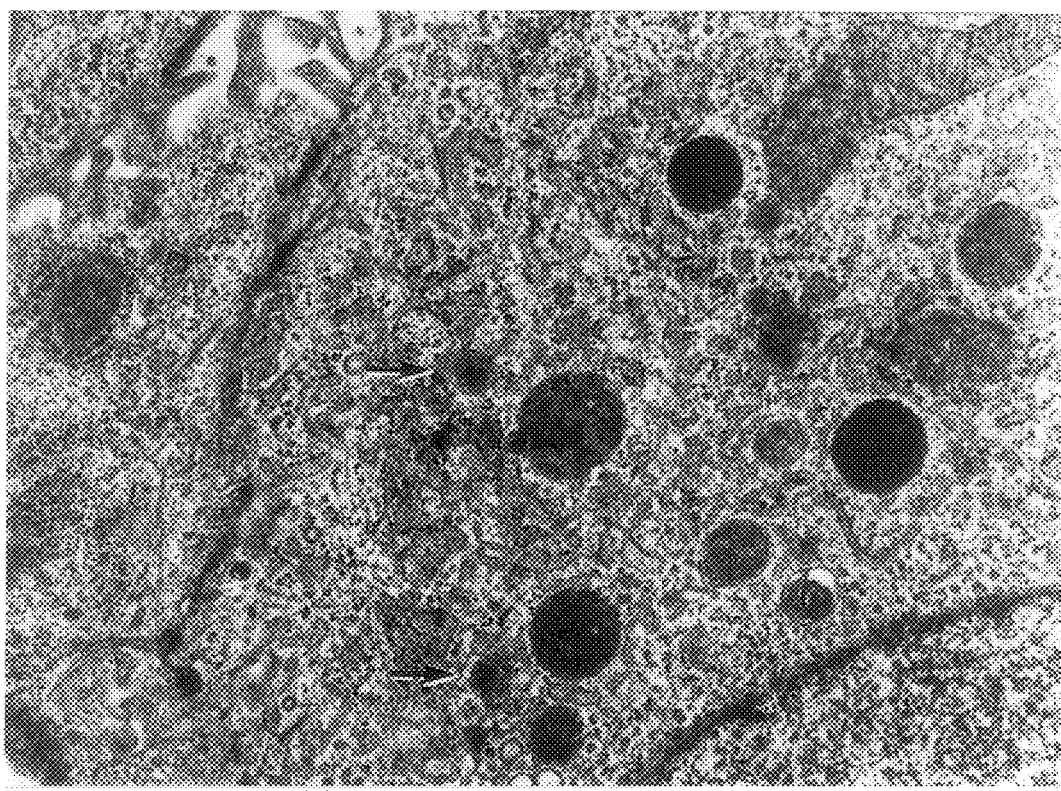

Finally, peroxisome which is a feature of hepatocyte was observed in the cytoplasm of the cells forming the colonies from the observation with a transmission electron microscope (FIGS. 38a and b).

Example 3

Liver paranchymal cells obtained by the same method as in EXAMPLE 2 were subcultured by the method of the present invention.

Culture medium was removed from the dish on which small hepatocytes form colonies, and the colonies were treated with 0.02% EDTA at 37° C. for about 10 minutes, thereby the colonies were detached from the dish. On replacing the colonies on a dish filled with the same medium as that for the primary culture, the small hepatocyte colonies and non-parenchymal cells around the colonies adhered on the dish and started to proliferate.

The liver parenchymal cells were subcultures by another procrdure. That is, after removing culture medium, the colonies were treated with 0.02% EDTA and 0.05% trypsin, thereby the colonies were dispersed into individuals of small hepatocytes and non-parenchymal cells. By pippetting the solution, small hepatocytes- and non-parenchymal cells- dispersed solution were obtained. Then, each of the solution was filtrated with 20 $\mu$m filter and aggergate of cells was removed, separated individuals of cell were obtained. The individuals of hepatocyte and non-parenchymal cell thus obtained were observed to adhere on dish, but only non-parenchymal cells proliferate in the same medium as that for the primary culture. In the conditioned medium of being used at the primary culture (1–4 days), small hepatocytes were observed to form a colony and proliferate. From these results, it was confirmed that the conditioned medium is necessary for subculturing small hepatocytes.

We claim:

1. A method for obtaining a liver parenchymal cell having a clonal growth ability and at least one of the following cell biological properties:

(i) presence of peroxysome;
   (ii) being positive to hepatocyte-markers;
   (iii) being partially positive to neoplastic hepatocyte-markers or immature hepatocyte-markers;
   (iv) being positive to antibodies against surface antigen of oval cells; and
   (v) being partially positive to bile duct cell-markers, which method comprises:
      (a) isolating hepatic cells from the liver of an adult mammal;
      (b) centrifuging the hepatic cells at low speed into heavy and light fractions;
      (c) culturing cells in the light fraction in a culture medium containing fetal bovine serum and ascorbic acid, wherein the cells are small hepatocytes and non-parenchymal cells; and
      (d) isolating one or more of small cells forming a colony to obtain the liver parenchymal cell having a clonal growth ability.

2. The method according to claim 1, wherein the small cells in the light fraction are cultured on DMEM medium containing fetal bovine serum, ascorbic acid, epidermal growth factor, nicotinamide and dimethyl sulfoxide.

3. The method according to claim 1, wherein the mammal is rat.

* * * * *